United States Patent
Tsai et al.

(10) Patent No.: US 10,927,138 B2
(45) Date of Patent: Feb. 23, 2021

(54) INHIBITORS OF D-AMINO ACID OXIDASE (DAAO) AND USES THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Ming-Hong Chien, New Taipei (TW); Tien-Lan Hsieh, New Taipei (TW)

(73) Assignee: SYNEURX INTERNATIONAL (TAIWAN) CORP., New Taipei (TW)

( * ) Notice: Subject to any disclaimer, the term of this patent is extended or adjusted under 35 U.S.C. 154(b) by 0 days.

(21) Appl. No.: 15/991,710

(22) Filed: May 29, 2018

(65) Prior Publication Data
US 2019/0367549 A1     Dec. 5, 2019

(51) Int. Cl.
| | |
|---|---|
| *C07H 15/18* | (2006.01) |
| *A61P 3/06* | (2006.01) |
| *A61P 3/04* | (2006.01) |
| *A61P 3/10* | (2006.01) |
| *A61P 25/00* | (2006.01) |

(52) U.S. Cl.
CPC ............ *C07H 15/18* (2013.01); *A61P 3/04* (2018.01); *A61P 3/06* (2018.01); *A61P 3/10* (2018.01); *A61P 25/00* (2018.01)

(58) Field of Classification Search
CPC .... C07H 15/18; A61P 3/04; A61P 3/06; A61P 3/10; A61P 25/00
USPC ......................................................... 514/25
See application file for complete search history.

(56) References Cited

U.S. PATENT DOCUMENTS

2007/0197610 A1* 8/2007 Kennis ................... A61K 31/42
                                                                          514/365
2017/0362394 A1* 12/2017 Chigurupati ......... A61K 38/018

FOREIGN PATENT DOCUMENTS

| WO | 200813047 A | 10/2008 |
|---|---|---|
| WO | 2013096182 A2 | 6/2013 |

OTHER PUBLICATIONS

Abdelwahed et al, Chemico-Biological Interactions, 2007, 165, 1-13.*
Sylla et al, Angew. Chem. Intl. Ed. 2015, 54, 8217-8221.*
Hu, Zhi Qing, et al.; "Mitogenic activity of (−)epigallocatechin gallate on B-cells and investigation of its structure-function relationship"; International Journal of Immunopharmacology 31; Dec. 31, 1992; No. 8 vol. 14; pp. 1399-1407.
Nishizawa, Makoto, et al.; "Structure of gallotannins in Paeoniae radix"; Chemical & Pharmaceutical Bulletin; Dec. 31, 1980; No. 9 vol. 28; pp. 2850-2852.
Sekowski, Szymon, et al.; "Interatction of a-synuclein with Rhus typhina tannin—Implication for Partkinson's disease"; Colloids and Surfaces; B: Biointerfaces; Apr. 10, 2017; vol. 155; pp. 159-165.
Sylla, Tahiri, et al.; "Gallotannins and Tannic Acid: First Chemical Syntheses and In Vitro Inhibitory Activity on Alzheimer's Amyloid B-Peptide Aggregation"; Angewandte Chemie, International Edition; May 26, 2015; No. 28 vol. 54; pp. 8217-8221.

* cited by examiner

*Primary Examiner* — Ganapathy Krishnan
(74) *Attorney, Agent, or Firm* — McDermott Will & Emery LLP

(57) ABSTRACT

Provided herein are compounds of Formula (I) and uses thereof for inhibiting the activity of D-amino acid oxidase (DAAO) or treating diseases or disorders associated with DAAO, such as a central nervous system (CNS) disorder, obesity, diabetes, or hyperlipidemia. Also provided in the present disclosure are methods of synthesizing the Formula (I) compounds described herein.

Formula (I)

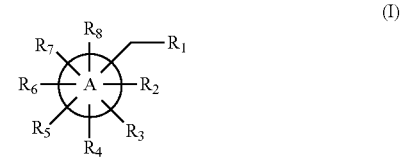

15 Claims, 1 Drawing Sheet

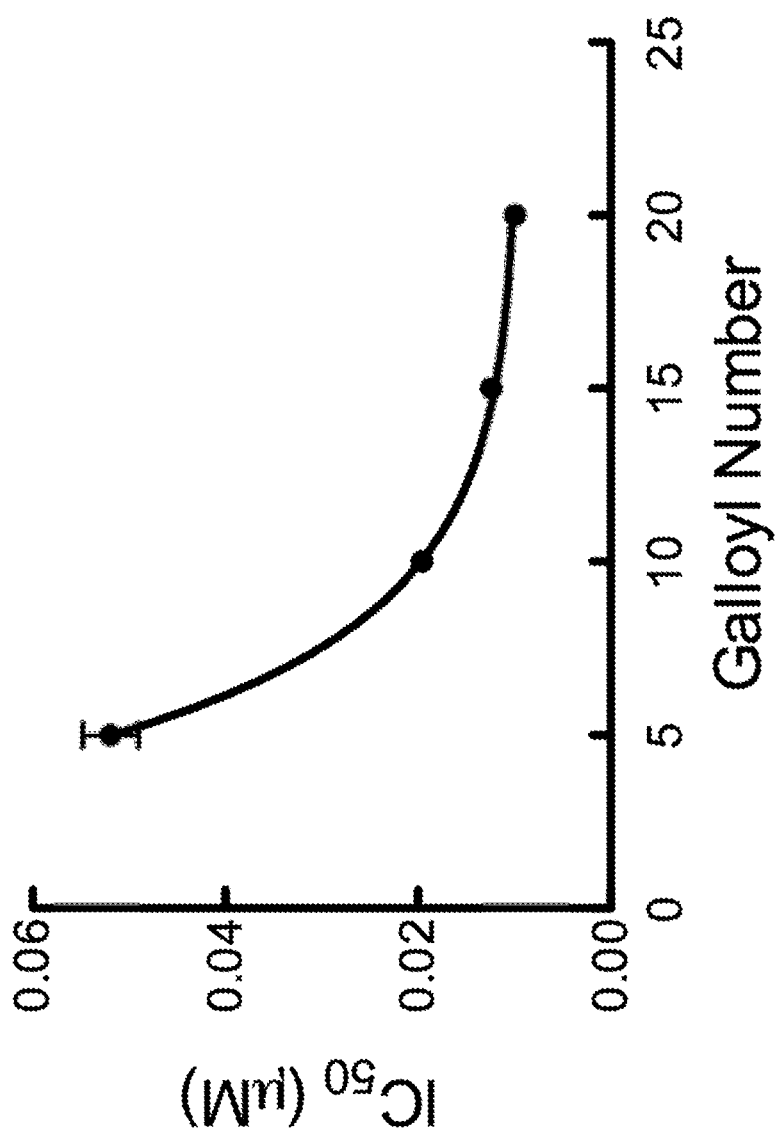

INHIBITORS OF D-AMINO ACID OXIDASE (DAAO) AND USES THEREOF

BACKGROUND OF THE INVENTION

The central nervous system (CNS) includes the brain and spinal cord. The CNS is vulnerable to various disorders, which may be caused by various factors, including genetic, trauma, infections, degeneration, structural defects and/or damage, tumors, blood flow disruption, and autoimmune disorders. Symptoms of a CNS disorder depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

N-methyl-D-aspartate (NMDA) receptor is a subtype glutamatergic receptor that plays a critical role in cognition, memory and neurotoxicity. Regulation of NMDA receptor is suggested to be beneficial for treating diseases of the central nervous system. D-amino acid oxidase (DAAO) is a peroxisomal enzyme that oxidizes D-amino acids to the corresponding imino acids. It has been reported that DAAO is involved in the metabolism of brain D-amino acids, including D-serine, and the regulation of the glutamatergic neurotransmission. As such, DAAO is a target for treating central nervous system (CNS) disorders that are associated with D-serine and/or glutamatergic neurotransmission. In addition, DAAO degrades D-serine to 3-hydroxypyruvate, a potential mediator of type II diabetes mellitus (Zhang, 2015). This suggests that DAAO inhibitors can be used to treat obesity, diabetes mellitus and hyperlipidemia.

SUMMARY OF THE INVENTION

The present disclosure is based on, at least in part, the development of the Formula (I) compounds described herein as effective DAAO inhibitors. Such compounds are expected to benefit treatment of diseases and disorders associated with DAAO and/or glutamatergic neurotransmission (e.g., obesity, diabetes, hyperlipidemia, or CNS disorders).

Accordingly, one aspect of the present disclosure provides a compound of formula (I):

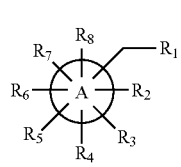

(I)

or a pharmaceutically acceptable salt thereof, wherein:
Ring A is a 5 to 8 membered monocyclic ring system, which optionally comprises at least one heteroatom selected from the group consisting of N, O, P, and S;
each of $R_1$, $R_2$, $R_3$, $R_4$, $R_5$, $R_6$, $R_7$, and $R_8$, independently, is absent, or of the formula:

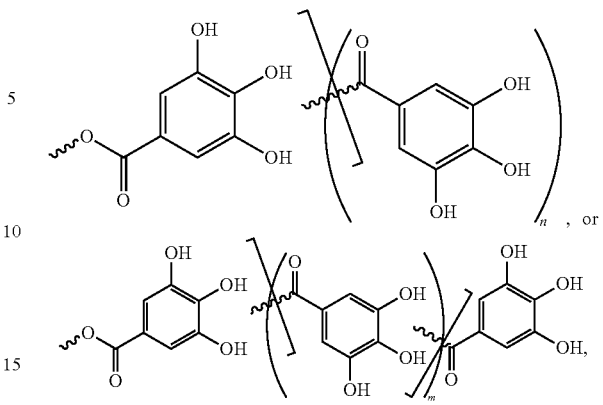

which is optionally substituted with 1, 2, 3, 4, or 5 substituents selected from the group consisting of $C_{1-3}$ alkyl, halogen, —CN, —NO$_2$, —SH, —S($C_{1-3}$ alkyl), —NH$_2$, NH($C_{1-3}$ alkyl), N($C_{1-3}$ alkyl)$_2$, and —O($C_{1-3}$ alkyl); wherein
n is 0 or 1;
m is 1, 2, 3, 4, or 5; and
the total number of galloyl moieties is an integer of 4 to 35, inclusive, and
wherein when the compound of Formula (I) is

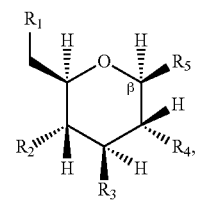

the total number of galloyl moieties is an integer of 15 to 35, inclusive.

In some embodiments, one, two, three, four, five, or six groups of $R_1$, $R_2$, $R_3$, $R_4$, $R_5$, $R_6$, $R_7$, and $R_8$, are absent.

In another aspect, the present disclosure provides compositions comprising the compound described herein and a carrier, which can be a pharmaceutical composition, a nutraceutical composition, a health food, or a medical food.

Also provided herein are methods for preparing the compound of formula (I) as described herein. Such a method may comprise the following steps:
(a) providing a compound of formula (Ia)

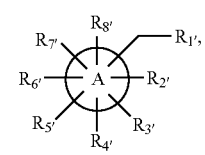

(Ia)

wherein $R_{1'}$, $R_{2'}$, $R_{3'}$, $R_{4'}$, $R_{5'}$, $R_{6'}$, $R_{7'}$, and $R_{8'}$, independently, are each —OH, —NH$_2$ or absent;
wherein
Ring A is a 5 to 8 membered monocyclic ring system, which optionally comprises at least one heteroatom selected from the group consisting of N, O, P, and S;

(b) reacting the compound of formula (Ia) with 7-(allyloxy)-2,2-diphenylbenzo[d][1,3]dioxole-5-carbonyl chloride, to allow conjugation of 7-(allyloxy)-2,2-diphenylbenzo[d][1,3]dioxole-5-carbonyl chloride to one or more of $R_{1'}$, $R_{2'}$, $R_{3'}$, $R_{4'}$, $R_{5'}$, $R_{6'}$, $R_{7'}$, and $R_{8'}$ of the compound of formula (Ia), thereby producing a first intermediate; and (c) de-protecting the allyl groups and the cyclic acetal groups in 7-(allyloxy)-2,2-diphenylbenzo[d][1,3]dioxole-5-carbonyl chloride that is conjugated to the compound of Formula (Ia) to obtain the compound of formula (I).

In some embodiments, one, two, three, four, five, or six groups of $R_{1'}$, $R_{2'}$, $R_{3'}$, $R_{4'}$, $R_{5'}$, $R_{6'}$, $R_{7'}$, and $R_{8'}$ are absent.

In yet another aspect, the present disclosure features a method for treating a disease or disorder associated with DAAO, the method comprising administering to a subject in need thereof an effective amount of a composition (e.g., a pharmaceutical composition, a health food product, or a medical food product), which comprises the compound described herein and (ii) a pharmaceutically acceptable carrier.

Also within the scope of the present disclosure are (i) any of the compounds of formula (I) described herein for use in treating an DAAO- and/or glutamatergic neurotransmission-associated disease/disorder, such as those described herein, or for treating an obesity disorder, eating disorder, anorexia nervosa, bulimia nervosa, hyperlipidemia, hyperglycemia, diabetes, or an CNS disorder, and (ii) uses of such the compound in manufacturing medicaments for use in treating any of the target diseases/disorders, including those described herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawing forms part of the present specification and is included to further demonstrate certain aspects of the present disclosure, which can be better understood by reference to the drawing in combination with the detailed description of specific embodiments presented herein.

FIG. 1 illustrates the human DAAO (hDAAO) inhibitory activities ($IC_{50}$, μM) of Examples 3, 4, and 5 of Formula (I).

DETAILED DESCRIPTION

Accordingly, the present disclosure provides compounds of Formula (I), which have 4 to 35 galloyl moieties linked to a ring system (e.g. glucose moiety); compositions containing any of the compounds of Formula (I) and a carrier; kits containing any of the compounds of Formula (I); methods for preparing the compounds of Formula (I) described herein; and methods of using such for inhibiting DAAO, thereby improving basic functioning, body weight, hyperactivity, anxiety, depression, suicidal ideation and/or behavior, sensorimotor gating, pain threshold, memory and cognitive behaviors in a subject in need of the treatment, and/or for treating diseases and disorders associated with DAAO, such as obesity disorders, hyperlipidemia, hypercholesterolemia, hyperglycemia, diabetes, and CNS disorders.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_3$-5, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl or substituted $C_{1-3}$ alkyl, e.g., —CF$_3$ or —CH$_2$OH).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g.,-CH=CHCH$_3$ or 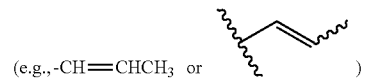 )

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

Alkyl, alkenyl, alkynyl, carbocyclyl, heterocyclyl, aryl, and heteroaryl groups, which are divalent bridging groups, are further referred to using the suffix—ene, e.g., alkylene, alkenylene, alkynylene, carbocyclylene, heterocyclylene, arylene, and heteroarylene.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R)$_2$, —C(=NRf)OR$^{ee}$, —OC(=NR)R$^{ee}$, —OC(=NR$^{ff}$)OR$^{ee}$, —C(=NR)N(R)$_2$, —OC(=NR)N(R)$_2$, —NR$^{ff}$C(=NR)N(R)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_1$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, and a carborane anion (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, —B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{c}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis,* T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), P-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —C(=O)S$R^{aa}$, —C(=O)$R^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy) methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl) methyl, 4,4',4"-tris(benzoyloxyphenyl)methyl, 3-(imidazol-1-yl)bis(4',4"-dimethoxyphenyl)methyl, 1,1-bis (4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy) butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference.

Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C$_{1-6}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkyl esters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "inhibition", "inhibiting", "inhibit," or "inhibitor" refer to the ability of a compound to reduce, slow, halt or prevent activity of a particular biological process in a cell relative to vehicle.

When a compound, pharmaceutical composition, method, use, or kit is referred to as "selectively," "specifically," or "competitively" binding a first protein, the compound binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a compound is referred to as "selectively," "specifically," or "competitively" modulating (e.g., increasing or inhibiting) the activity of a protein, the compound modulates the activity of the protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease. In certain embodiments, a subject is a human of having, or at risk for a central nervous system (CNS) disorder, obesity, diabetes, or hyperlipidemia.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neuropsychiatric disorder," including either neurological diseases or psychiatric disorders or CNS (central nervous system) disorders, or refers to a disorder that involves either behavioral or psychiatric symptoms or syndromes caused by neurodegenerative or organic brain disorders. The main characteristics of neuropsychiatric symptoms include occurrence of the various psychiatric symptoms, cognitive impairment, neurological symptoms or the possibility of early cerebral development symptoms. For example, the neuropsychiatric disorder can include, but is not limited to, schizophrenia, psychotic disorders, major depressive disorder, suicidal ideation and/or behavior, Alzheimer's disease, dementia, frontotemporal dementia, mild cognitive impairment, benign forgetfulness, closed head injury, an autistic spectrum disorder, Asperger's disorder, Fragile X syndrome, attention deficit hyperactivity disorders, combined attention-deficit hyperactivity disorder and tic disorder, obsessive compulsive disorder, tic disorders, Tourette's syndrome, childhood learning disorders, premenstrual syndrome, depression, bipolar disorders, anxiety disorders, panic disorders, post-traumatic stress disorder, chronic pain, eating disorders, addiction disorders, personality disorders, Parkinson's disorder, Huntington's disorder, amyotrophic lateral sclerosis, nocturnal enuresis, stroke, Duchenne muscular dystrophy, blepharospasm and non-epileptic seizures.

The term "neurological disease" refers to any disease of the nervous system, including diseases that involve the central nervous system (brain, brainstem, spinal cord and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, frontotemporal dementia, Parkinson's disease, amyotrophic lateral sclerosis, tauopathies (including frontotemporal dementia), multiple system atrophy, and Huntington's disease. Examples of neurological diseases include, but are not limited to, headache, stupor and coma, dementia, seizure, sleep disorders, trauma, infections, neoplasms, neuro-ophthalmopathy, movement disorders, demyelinating diseases, spinal cord disorders, and disorders of peripheral nerves, muscle and neuromuscular junctions. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; chronic pain; Batten disease; Behcet's disease; Bell's palsy; benign essential blepharospasm; benign focal amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal cord tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to mental disorders and includes diseases and disorders listed in the Diagnostic and Statistical Manual of Mental Disorders—Fourth Edition and Fifth Edition (DSM-IV, DSM-V), published by the American Psychiatric Association, Washington D.C. (1994, 2015). Psychiatric disorders include, but are not limited to, anxiety disorders (e.g., acute stress disorder, agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder I and II, cyclothymic disorder, dysthymic disorder, and major depressive disorder), suicidal ideation and/or behavior, personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence or abuse, amphetamine dependence or abuse, cannabis dependence or abuse, cocaine dependence or abuse, hallucinogen dependence or abuse, inhalant dependence or abuse, nicotine dependence or abuse, opioid dependence or abuse, phencyclidine dependence or abuse, and sedative dependence or abuse), adjustment disorders, autism, Asperger's disorder, autistic disorder, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperlipidemia, hyperinsulinemia, insulin resistance, and obesity.

The terms "health food" or "health food product" refers to any kind of liquid and solid/semi-solid materials that are used for nourishing humans and animals, for improving basic behavioral functioning, hyperactivity, anxiety, depression, suicidal ideation and/or behavior, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The term "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

Compounds of Formula (I)

One aspect of the present disclosure relates to a compound of formula (I):

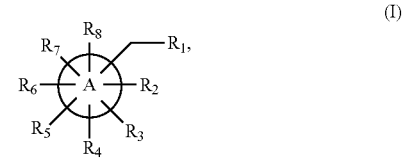

or a pharmaceutically acceptable salt thereof, wherein:
Ring A is a 5 to 8 membered monocyclic ring system, which optionally comprises at least one heteroatom selected from the group consisting of N, O, P, and S; each of $R_1$, $R_2$, $R_3$, $R_4$, $R_5$, $R_6$, $R_7$, and $R_8$, independently, is absent, or of the formula:

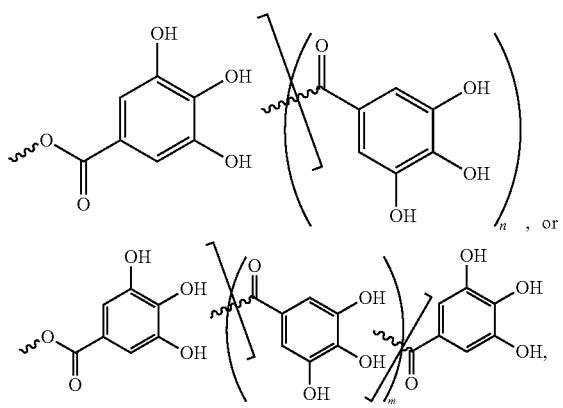

which is optionally substituted with 1, 2, 3, 4, or 5 substituents selected from the group consisting of $C_{1-3}$ alkyl, halogen, —CN, —NO$_2$, —SH, —S($C_{1-3}$ alkyl), —NH$_2$, NH($C_{1-3}$ alkyl), N($C_{1-3}$ alkyl)$_2$, and —O($C_{1-3}$ alkyl); wherein n is 0 or 1;
m is 1, 2, 3, 4, or 5; and
the total number of galloyl moieties is an integer of 4 to 35, inclusive, and
wherein when the compound of Formula (I) is

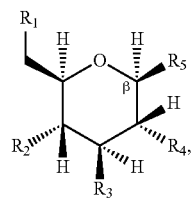

the total number of galloyl moieties is an integer of 15 to 35, inclusive.

In some embodiments, one of $R_1$, $R_2$, $R_3$, $R_4$, $R_5$, $R_6$, $R_7$, and $R_8$ is absent. In some embodiments, two of $R_1$, $R_2$, $R_3$, $R_4$, $R_5$, $R_6$, $R_7$, and $R_8$ are absent. In some embodiments, three of $R_1$, $R_2$, $R_3$, $R_4$, $R_5$, $R_6$, $R_7$, and $R_8$ are absent. In some embodiments, four of $R_1$, $R_2$, $R_3$, $R_4$, $R_5$, $R_6$, $R_7$, and $R_8$ are absent. In some embodiments, five of $R_1$, $R_2$, $R_3$, $R_4$, $R_5$, $R_6$, $R_7$, and $R_8$ are absent. In some embodiments, six of $R_1$, $R_2$, $R_3$, $R_4$, $R_5$, $R_6$, $R_7$, and $R_8$ are absent. In some embodiments, seven of $R_1$, $R_2$, $R_3$, $R_4$, $R_5$, $R_6$, $R_7$, and $R_8$ are absent.

In some embodiments, the total number of galloyl moieties of the compound of Formula (I) described herein is an integer of 4 to 35, inclusive. In some embodiments, the total number of galloyl moieties of the compound of Formula (I) described herein is an integer of 15 to 35, inclusive. In some embodiments, when the compound of Formula (I) is

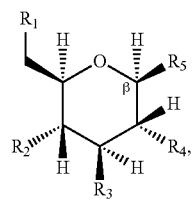

the total number of galloyl moieties is an integer of 15 to 35, inclusive. In some embodiments, the total number of galloyl moieties of the compound of Formula (I) described herein is an integer of 15 to 25, inclusive. In some embodiments, the total number of galloyl moieties of the compound of Formula (I) described herein is an integer of 20 to 25, inclusive. In some embodiments, the total number of galloyl moieties of the compound of Formula (I) described herein is an integer of 15 to 20, inclusive. In some embodiments, the total number of galloyl moieties of the compound of Formula (I) described herein is an integer of 25 to 35, inclusive. In some embodiments, the total number of galloyl moieties of the compound of Formula (I) described herein is an integer of 20 to 30, inclusive. In some embodiments, the total number of galloyl moieties of the compound of Formula (I) described herein is an integer of 30 to 35, inclusive. In some embodiments, the total number of galloyl moieties of the compound of Formula (I) described herein is 30. In some embodiments, the total number of galloyl moieties of the compound of Formula (I) described herein is 35. In some embodiments, the total number of galloyl moieties of the compound of Formula (I) described herein is 15, 20, 25, or 30.

In some embodiments, Ring A is a 5-8 membered monocyclic ring system (e.g., having 6 pi electrons shared in a cyclic array), which optionally comprises at least one ring heteroatoms provided in the ring system, wherein each heteroatom is independently selected from nitrogen, oxygen, phosphorus, and sulfur ("5-8 membered heterocyclic ring"). In some embodiments, Ring A is a 5-8 membered ring system having no heteroatom. In some embodiments, Ring A is a 5-8 membered ring system having ring carbon atoms and at least one ring heteroatoms provided in the ring system, wherein each heteroatom is independently selected from the group consisting of nitrogen, oxygen, phosphorus, and sulfur ("5-8 membered heterocyclic ring"). In some embodiments, Ring A is a 5-6 membered heterocyclic ring system having ring carbon atoms and at least one ring heteroatoms provided in the ring system, wherein each heteroatom is independently selected from the group consisting of nitrogen, oxygen, phosphorus, and sulfur ("5-6 membered heterocyclic ring"). In some embodiments, Ring A is a 5-6 membered heterocyclic ring with 1 ring heteroatom selected from the group consisting of nitrogen, oxygen, phosphorus and sulfur. In some embodiments, Ring A is a 5-8 membered heterocyclic ring with at least one oxygen. In some embodiments, Ring A is a 5-6 membered heterocyclic ring with at least one oxygen.

In some embodiments, Ring A is

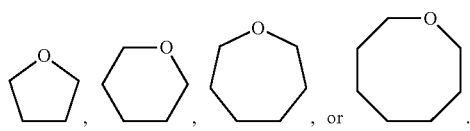

In some embodiments, Ring A is

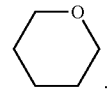

In some embodiments, each of $R_1$, $R_2$, $R_3$, $R_4$, $R_5$, $R_6$, $R_7$ and $R_8$ is independently selected from the group consisting of

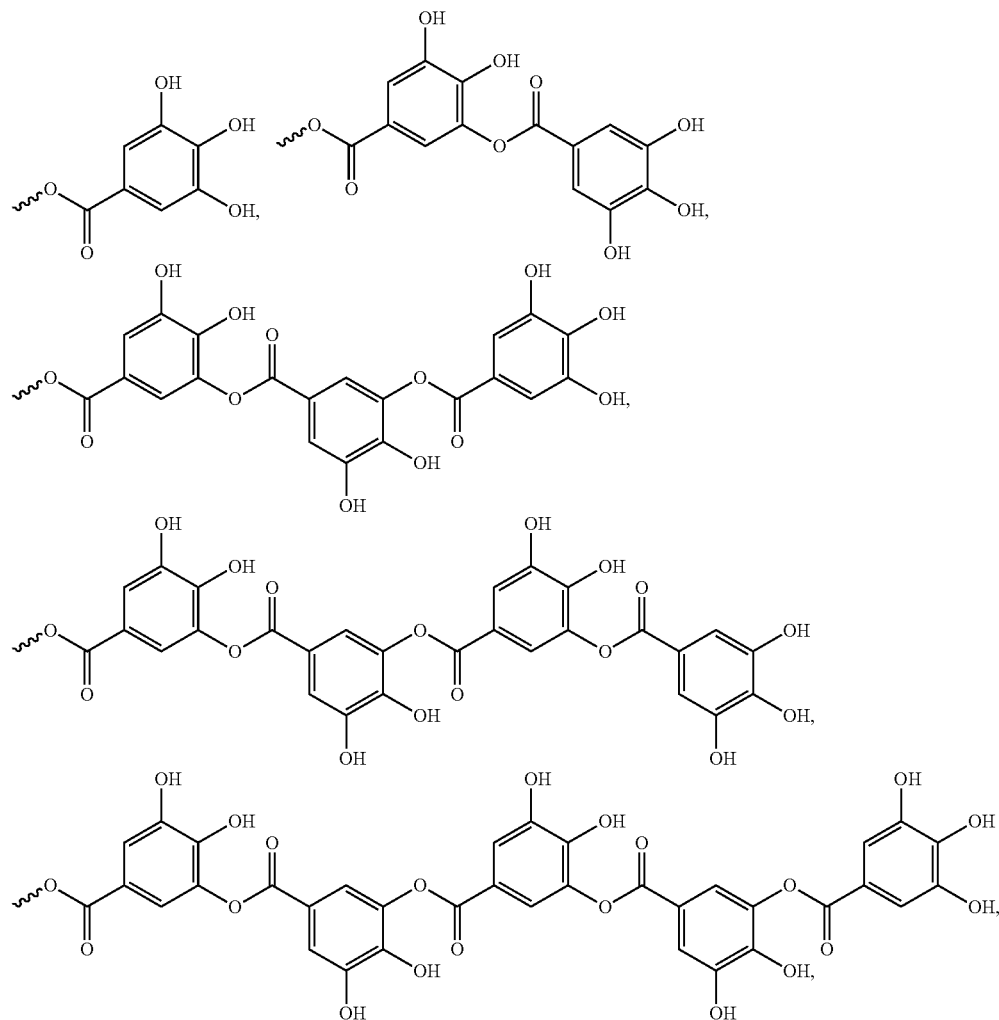
and absent. In some embodiments, at least one instance of $R_1$, $R_2$, $R_3$, $R_4$, $R_5$, $R_6$, $R_7$, or $R_8$ is independently
In some embodiments, at least one instance of $R_1$, $R_2$, $R_3$, $R_4$, $R_5$, $R_6$, $R_7$, or $R_8$ is independently
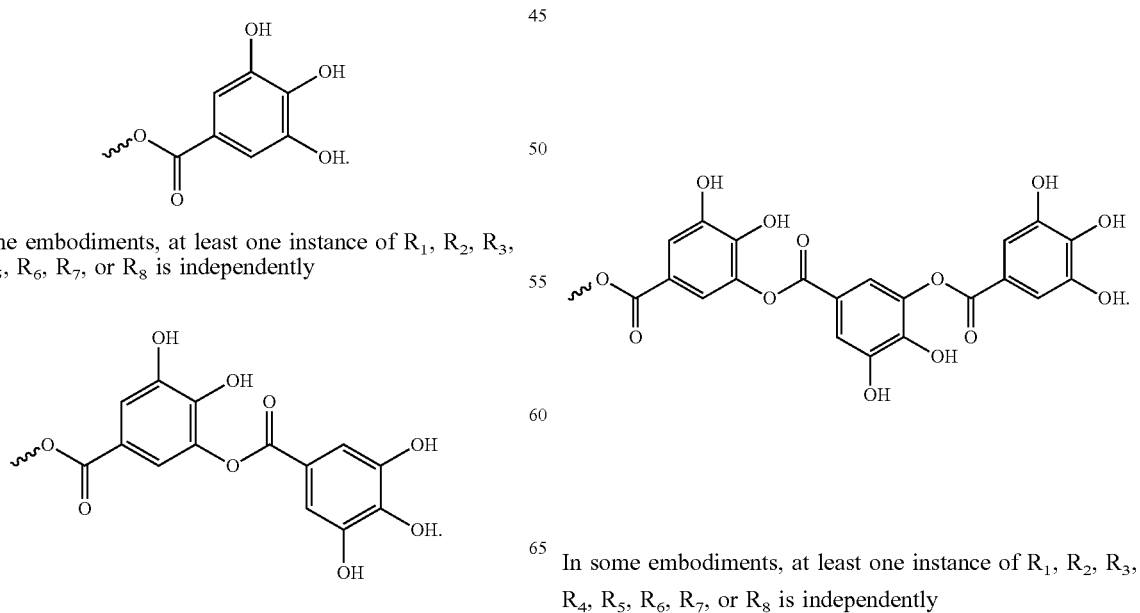
In some embodiments, at least one instance of $R_1$, $R_2$, $R_3$, $R_4$, $R_5$, $R_6$, $R_7$, or $R_8$ is independently

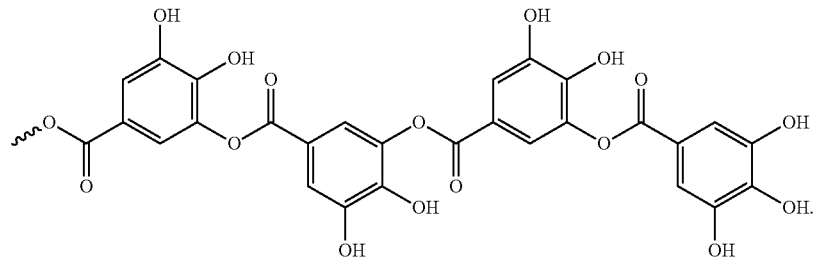

In some embodiments, at least one instance of $R_1$, $R_2$, $R_3$, $R_4$, $R_5$, $R_6$, $R_4$, or $R_8$ is independently

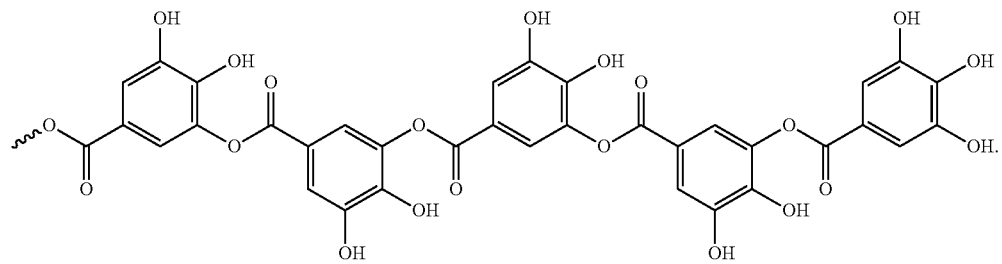

In some embodiments, at least one instance of $R_1$, $R_2$, $R_3$, $R_4$, $R_5$, $R_6$, $R_4$, or $R_8$ is independently absent.

In some embodiments, each of $R_1$, $R_2$, $R_3$, $R_4$, $R_5$, $R_6$, $R_4$, and $R_8$, independently, is or of the formula:

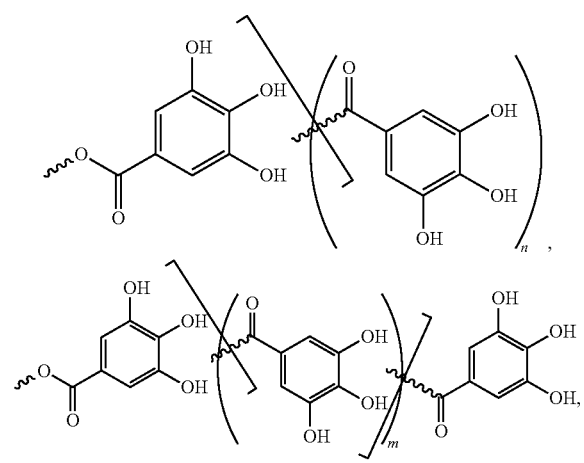

or absent. In some embodiments, at least one instance of $R_1$, $R_2$, $R_3$, $R_4$, $R_5$, $R_6$, $R_7$, or $R_8$ is

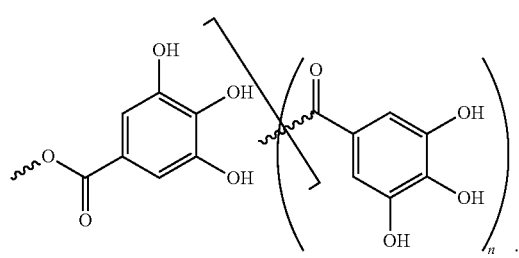

In some embodiments, at least one instance of $R_1$, $R_2$, $R_3$, $R_4$, $R_5$, $R_6$, $R_7$, or $R_8$ is

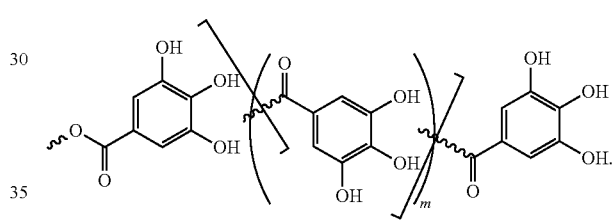

In some embodiments, at least one instance of $R_1$, $R_2$, $R_3$, $R_4$, $R_5$, $R_6$, $R_4$, or $R_8$ is absent.

In some embodiments, each of $R_1$, $R_2$, $R_3$, $R_4$, $R_5$, $R_6$, $R_7$, and $R_8$ is optionally substituted with 1, 2, 3, 4, or 5 substituents selected from the group consisting of $C_{1-3}$ alkyl, halogen, —CN, —NO$_2$, —SH, —S($C_{1-3}$ alkyl), —NH$_2$, NH($C_{1-3}$ alkyl), N($C_{1-3}$ alkyl)$_2$, and —O($C_{1-3}$ alkyl). In some embodiments, at least one of $R_1$, $R_2$, $R_3$, $R_4$, $R_5$, $R_6$, $R_7$, and $R_8$ is optionally substituted with $C_{1-3}$ alkyl (e.g., unsubstituted methyl, unsubstituted ethyl, or unsubstituted n-propyl). In some embodiments, at least one of $R_1$, $R_2$, $R_3$, $R_4$, $R_5$, $R_6$, $R_7$, and $R_8$ is optionally substituted with halogen (e.g., F, Cl, or Br). In some embodiments, at least one of $R_1$, $R_2$, $R_3$, $R_4$, $R_5$, $R_6$, $R_7$, and $R_8$ is optionally substituted with —CN, —NO$_2$, —SH, —S($C_{1-3}$ alkyl), —NH$_2$, NH($C_{1-3}$ alkyl), N($C_{1-3}$ alkyl)$_2$, or —O($C_{1-3}$ alkyl). In some embodiments, $C_{1-3}$ alkyl is unsubstituted methyl, unsubstituted ethyl, or unsubstituted n-propyl. In some embodiments, n is 0 or 1. In some embodiments, n is 0. In some embodiments, n is 1. In some embodiments, m is 1, 2, 3, 4, or 5. In some embodiments, m is 1. In some embodiments, m is 2. In some embodiments, m is 3. In some embodiments, m is 4. In some embodiments, m is 5.

In some embodiments, the compound of formula (I) is of the formula:
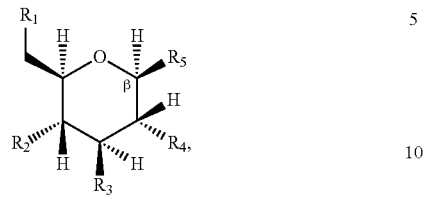
and each of $R_1$, $R_2$, $R_3$, $R_4$, and $R_5$, independently, are each selected from the group consisting of:
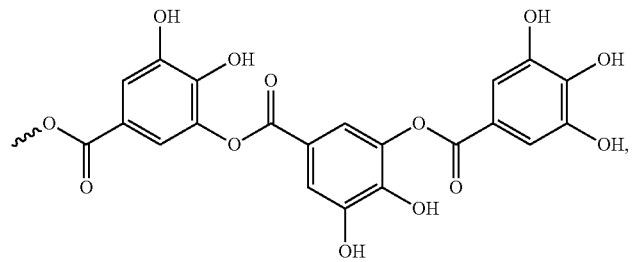
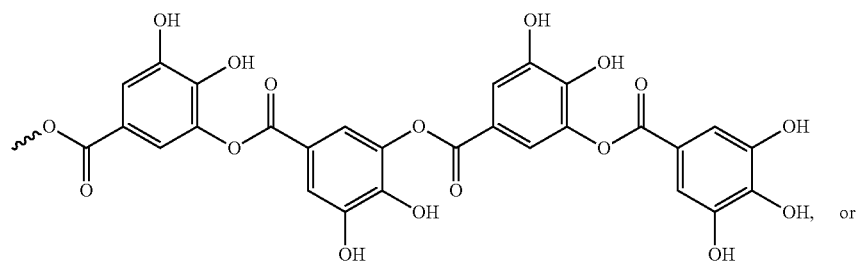
or
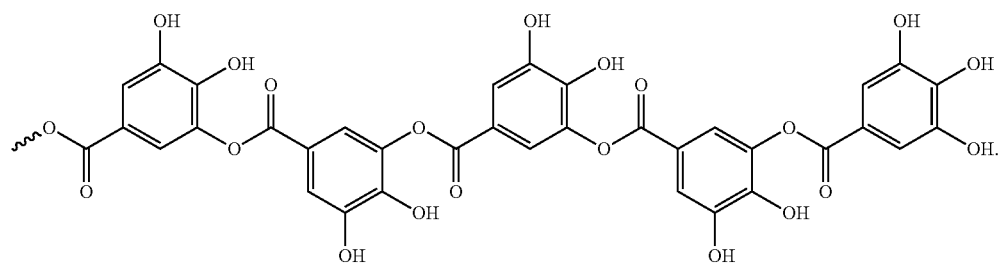
In some embodiments, the compound of formula (I) is of the formula:
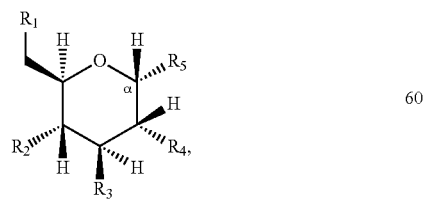
and each of $R_1$, $R_2$, $R_3$, $R_4$, and $R_5$, independently, are each selected from the group consisting of:

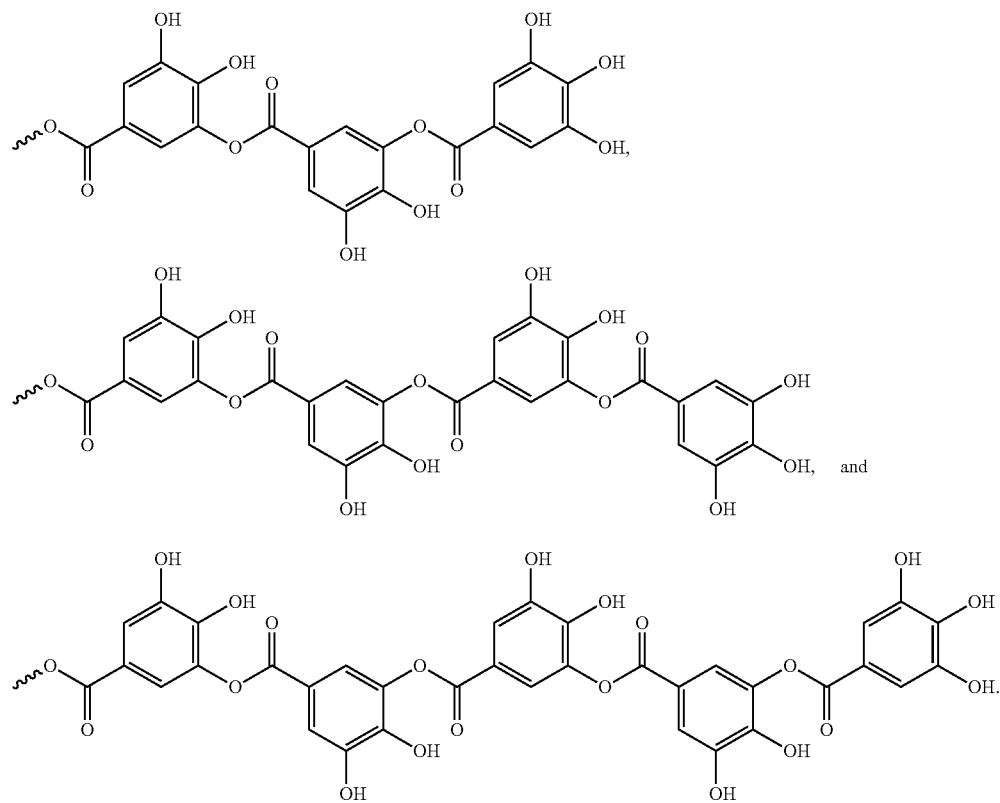
In some embodiments, the compound of formula (I) is: compound 13, compound 16, compound 23, or a pharmaceutically acceptable salt thereof. In some embodiments, the compound of formula (I) is not compound 10. In some embodiments, the compound of formula (I) is: compound 23, or a pharmaceutically acceptable salt thereof.
In some embodiments, the compound of formula (I) is of the formula:
13
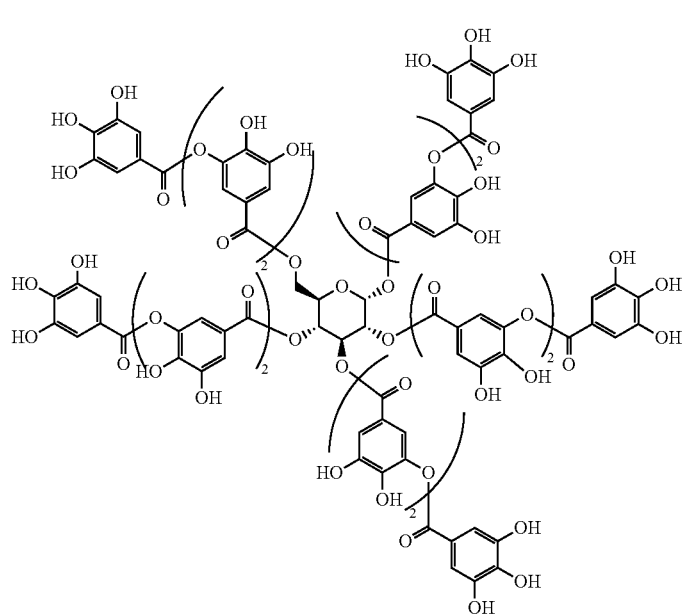

16

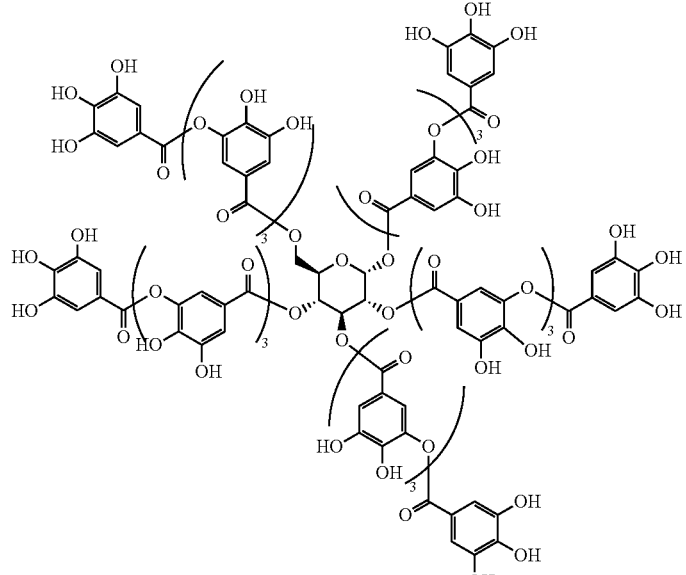

23

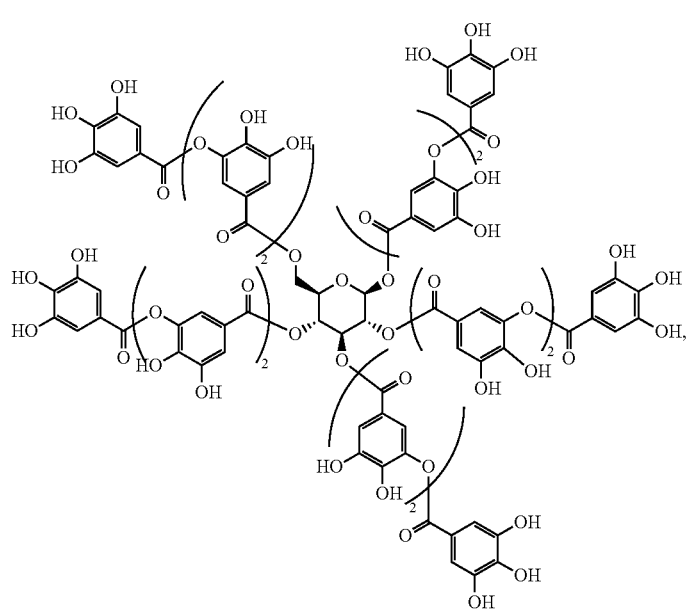

or a pharmaceutically acceptable salt thereof. In some embodiments, the compound of formula (I) is compound 101, compound 102, compound 103, compound 13 (the compound product of Example 3), compound 16 (the compound product of Example 4), or compound 23 (the compound product of Example 5) (Table 1). In some embodiments, the compound of formula (I) is a compound in Table 1 below.

Compounds of Formula (I)

The compositions described herein comprise one or more compounds of Formula (I) described herein or pharmaceutically acceptable salts thereof. The term "pharmaceutically-acceptable salts" refers to a relatively non-toxic, inorganic, or organic base addition salts of the compounds of Formula (I). These salts can be prepared in situ in the administration vehicle or the dosage form manufacturing process, or by separately reacting the one or more compounds of Formula (I) described herein with a suitable organic or inorganic base, and isolating the salt thus formed during subsequent purification. Suitable inorganic bases include, but are not limited to, sodium hydroxide, barium hydroxide, iron(II) hydroxide, iron(III) hydroxide, magnesium hydroxide, calcium hydroxide, aluminum hydroxide, ammonium hydroxide, potassium hydroxide, cesium hydroxide, or lithium hydroxide. Suitable organic bases include, but are not limited to, pyridine, methyl amine, imidazole, benzimidazole, histidine, phosphazene bases, or a hydroxide of an organic cation such as quaternary ammonium hydroxide and phosphonium hydroxide. See, for example, Berge et al. (1977) J. Pharm. Sci. 66:1-19.

The compounds of Formula (I) described herein may be subjected to one or more purification procedures, for example, re-crystallization and chromatography (e.g., flash column chromatography) or a combination thereof. See, e.g., Examples below.

Compositions of Compounds of Formula (I) and Kits Containing Such

Any of the compounds described herein may be formulated to form a pharmaceutical composition, a nutraceutical composition, a health food, or a medical food. Another aspect of the present disclosure relates to compositions, for example, pharmaceutical compositions, health food product such as nutraceutical compositions, and medical food that comprise one or more compounds of Formula (I) described herein and a carrier, e.g., a pharmaceutically acceptable carrier and/or an edible carrier. Such carriers, either naturally occurring or non-naturally occurring (synthetic), may confer various benefits to the compounds of Formula (I) in the composition, for example, improving in vitro and/or in vivo stability of the compounds of Formula (I), enhancing bioavailability of the compounds of Formula (I), increasing bioactivity of the compounds of Formula (I), and/or reducing side effects. In some embodiments, provided herein is a composition comprising a compound of Formula (I) and a carrier. In some embodiments, the composition is a pharmaceutical composition, a nutraceutical composition, a health food, or a medical food. Suitable carriers include, but are not limited to, diluents, fillers, salts, buffers, stabilizers, solubilizers, buffering agents, preservatives, or a combination thereof. In some examples, the carrier may comprise benzoate such as sodium benzoate.

Pharmaceutical Compositions

In some embodiments, the one or more compounds of Formula (I) described herein can be mixed with a pharmaceutically acceptable carrier (excipient) to form a pharmaceutical composition, which can be used for treating any of the target diseases as described herein. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

Pharmaceutically acceptable carriers include diluents, fillers, salts, buffers, stabilizers, solubilizers and other material which are well-known in the art. Exemplary pharmaceutically acceptable carriers for the compounds of Formula (I) or salts thereof in particular are described in the U.S. Pharmacopeia U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from a suitable inorganic base, (e.g., sodium hydroxide, barium hydroxide, iron (II) hydroxide, iron(III) hydroxide, magnesium hydroxide, calcium hydroxide, aluminium hydroxide, ammonium hydroxide, potassium hydroxide, cesium hydroxide, or lithium hydroxide) or a suitable organic base (e.g., pyridine, methyl amine, imidazole, benzimidazole, histidine, phosphazene bases, or a hydroxide of an organic cation such as quaternary ammonium hydroxide and phosphonium hydroxide). Also, pharmaceutically-acceptable salts can be prepared as alkaline metal or alkaline earth salts, such as lithium, sodium, potassium or calcium salts.

The compositions comprising compounds described herein can comprise pharmaceutically acceptable carriers, excipients, or stabilizers in the form of lyophilized formulations or aqueous solutions. Remington: The Science and Practice of Pharmacy 20th Ed. (2000) Lippincott Williams and Wilkins, Ed. K. E. Hoover. Such carriers, excipients or stabilizers may enhance one or more properties of the active ingredients (e.g., the compounds of Formula (I)) in the compositions described herein), e.g., bioactivity, stability, bioavailability, and other pharmacokinetics and/or bioactivities.

Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ (polysorbate), PLURONICS™ (nonionic surfactants), or polyethylene glycol (PEG).

In other examples, the pharmaceutical composition described herein can be formulated in a sustained-release format. Suitable examples of sustained-release preparations include semipermeable matrices of solid hydrophobic polymers containing the compounds of Formula (I) described herein, which matrices are in the form of shaped articles, e.g., films, or microcapsules. Examples of sustained-release matrices include, but are not limited to, polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the pharmaceutical compositions used for in vivo administration are sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation, or intrathecal or intracerebral routes.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 1000 mg of the active ingredient of the present invention. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

In some embodiments, any of the compositions comprising compounds described herein may further comprise a second therapeutic agent based on the intended therapeutic uses of the composition.

In some embodiments, the second therapeutic agent is an anti-obesity agent, including, but not limited to, orlistat, lorcaserin, sibutramine, rimonabant, metformin, exenatide, pralintide, phentermine, fenfluramine, dexfenfluramine, topiramate, dinitrophenol, bupropion, and zonisamide.

In some embodiments, the second therapeutic agent is an agent for treating a CNS disease/disorder. In some embodiments, the second therapeutic agent can be an antidepressant, an antipsychotic, a psychostimulant, a mood stabilizer, an anxiolytic, an agent for treating attention deficit hyperactivity disorder (ADHD), or an agent for treating Alzheimer's disease (AD).

Exemplary antipsychotic drugs include, but are not limited to, butyrophenone (e.g., haloperidol (HALDOL™), phenothiazine (e.g., chlorpromazine (THORAZINE™), fluphenazine (PROLIXIN™), perphenazine (TRILAFON™), prochlorperazine (COMPAZINE™), thioridazine (MELLARIL™), trifluoperazine (STELAZINE™), mesoridazine, promazine, triflupromazine (VESPRIN™), levomepromazine (NOZINAN™), promethazine (PHENERGAN™), thioxanthene (e.g., chlorprothixene, flupenthixol (DEPIXOL™ FLUANXOL™)), thiothixene (NAVANE™), zuclopenthixol (CLOPIXOL™, ACUPHASE™), clozapine (CLOZARIL™), olanzapine (ZYPREXA™), risperidone (RISPERDAL™ RISPERDAL CONSTA™), quetiapine (SEROQUEL™), ziprasidone (GEODON™), amisulpride (SOLIAN™), asenapine, paliperidone (INVEGA®), aripiprazole (ABILIFY™), dopamine partial agonists (BIFEPRUNOX™, NORCLOZAPINE™ (ACP-104)), lamotrigine (LAMICTAL™), cannabidiol, LY2140023, droperidol, pimozide, butaperazine, carphenazine, remoxipride, piperacetazine, sulpiride, acamprosate, tetrabenazine (NITOMAN™ XENAZINE™) and the like.

Alternatively, the second therapeutic agent can be an antidepressant and/or mood stabilizer. In certain embodiments the antidepressant comprises a monoamine oxidase inhibitor (MAOI), a tricyclic antidepressant (TCA), a tetracyclic antidepressant (TeCA), a selective serotonin reuptake inhibitor (SSRI), a noradrenergic and specific serotonergic antidepressant (NASSA), a norepinephrine (noradrenaline) reuptake inhibitor, a norepinephrine-dopamine reuptake inhibitor, a serotonin-norepinephrine-dopamine reuptake inhibitor (SNDRI), a serotonin-norepinephrine reuptake inhibitor (SNRI), mood stabilizer, and/or monoamine oxidase inhibitor (MAOI). Exemplary SSRIs include fluoxetine (PROZAC™), paroxetine (PAXIL™ SEROXAT™), escitalopram (LEXAPRO™, ESIPRAM™), citalopram (CELEXA™), sertraline (ZOLOFT™), fluvoxamine (LUVOX™)). Exemplary SNRIs include venlafaxine (EFFEXOR™), milnacipram and duloxetine (CYMBALTA™). Additional antidepressant include a noradrenergic and specific serotonergic antidepressant (NASSA) (e.g., mirtazapine (AVANZA™, ZISPIN™, REMERON™), or mianserin, a norepinephrine (noradrenaline) reuptake inhibitor (NRI) (e.g., reboxetine (EDRONAX™)), a norepinephrine-dopamine reuptake inhibitors (e.g., bupropion (WELLBUTRIN™, ZYBAN™)), amitriptyline, nortriptiline, protriptyline, desipramine, imipramine, trimipramine, amoxapine, bupropion, bupropion SR, clomipramine, doxepin, isocarboxazid, venlafaxine XR, tranylcypromine, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, isoniazid, iproniazid, and the like.

In some embodiments, the second therapeutic agent can be an agent for the treatment of ADD and/or ADHD. Suitable ADHD medications include, but are not limited to amphetamine, modafinil, desoxyn, methamphetamine, cocaine, arecoline, dexmethylphenidate (focalin, focalin XR), dextroamphetamine (dexedrine, dexedrine spansules, dextroamphetamine ER, dextrostat), methylphenidate (concerta, daytrana, metadate CD, metadate ER, methylin, methylin ER, ritalin, ritalin-LA, ritalin-SR), lisdexamfetamine dimesylate (Vyvanse), mixed salts amphetamine (Adderall, Adderall XR), atomoxetine (Strattera), clonidine hydrochloride (Catapres), guanfacine hydrochloride (Tenex), arecoline, and pemoline.

Further, in some embodiments, the second therapeutic agent may be an agent for use in treating a cognitive disorder, and/or a condition characterized by neurodegeneration (e.g., Alzheimer's disease, or Parkinson's disease). Such therapeutic agents include, but are not limited to tacrine, rivastigmine, donepezil (Aricept™), physostigmine, nicotine, arecoline, huperzine alpha, selegiline, Rilutek™ (riluzole), memantine (AXURA™, AKATINOL™ NAMENDA™, EBIXA™, ABIXA™), vitamine c, vitamine e, carotenoids, *Ginkgo biloba,* and the like.

Health Food Products

In some embodiments, the compositions described herein can be a health food or a health food product, which can be any kinds of liquid and solid/semi-solid materials that are used for nourishing humans and animals, for improving basic behavioral functioning, hyperactivity, anxiety, depression, suicidal ideation and/or behavior, sensorimotor gating, pain threshold, memory and/or cognitive functioning, or for facilitating treatment of any of the target diseases noted herein (e.g., an obesity disorder, hyperlipidemia, hyperglycemia, diabetes, or a CNS disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, containing one or more compounds of Formula (I), may comprise one or more edible carriers, which confer one or more of the benefits to the compounds of Formula (I) in the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the healthy food products described herein may further include neuroprotective foods, such as fish oil, flax seed oil, and/or benzoate.

In some examples, the healthy food product is a nutraceutical composition, which refers to compositions containing components from food sources and conferring extra health benefits in addition to the basic nutritional value found in foods. A nutraceutical composition as described herein comprises the compound of Formula (I) content described herein and additional ingredients and supplements that promote good health and/or enhance stability and bioactivity of the compounds of Formula (I).

The actions of nutraceutical compositions may be fast or/and short-term or may help achieve long-term health objectives as those described herein, e.g., improving basic behavioral functioning, hyperactivity, anxiety, depression, suicidal ideation and/or behavior, sensorimotor gating, pain threshold, memory and/or cognitive functioning in, e.g., human subjects who have or are at risk for diseases associated with DAAO such as CNS disorders or human subjects who have or are at risk for an obesity disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

The health food products described herein may further comprise one or more second therapeutic agents, including those described herein.

Medical Food Products

In certain embodiments, the composition is a medical food, which may be a food product formulated to be consumed or administered enterally. In certain embodiments, the medical food is used for improving basic behavioral functioning, hyperactivity, anxiety, depression, suicidal ideation and/or behavior, sensorimotor gating, pain threshold, memory and/or cognitive functioning, and/or for treating a target disease as described herein (e.g., an obesity disorder, hyperlipidemia, hyperglycemia, diabetes, or a CNS disorder). Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management.) In some examples, a medical food composition described herein is not one of those that would be simply recommended by a physician as part of an overall diet to manage the symptoms or reduce the risk of a disease or condition.

Any of the medical food compositions described herein, comprising one or more compounds of Formula (I) molecules or salts thereof and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the compound of Formula (I) content in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

Kits

The present disclosure also provides kits for use in treating any of the target disorders described herein. In some embodiments, the kits are for use in improving basic behavioral functioning, hyperactivity, anxiety, depression, suicidal ideation and/or behavior, sensorimotor gating, pain threshold, memory and/or cognitive functioning, and/or for treating a target disease as described herein (e.g., an obesity disorder, hyperlipidemia, hyperglycemia, diabetes, or a CNS disorder). Such kits can include one or more containers comprising a composition comprising a compound of Formula (I) as described herein and optionally one or more of the second therapeutic agents as also described herein.

In some embodiments, the kit can comprise instructions for use in accordance with any of the methods described herein. The included instructions can comprise, for example, a description of administration of composition comprising a compound of Formula (I) and optionally a description of administration of the second therapeutic agent(s) to improve basic behavioral functioning, hyperactivity, anxiety, depression, suicidal ideation and/or behavior, sensorimotor gating, pain threshold, memory and/or cognitive functioning, or to treat a target disease as described herein. The kit may further comprise a description of selecting an individual suitable for treatment based on identifying whether that individual has the disease or is at risk for the disease. In still other embodiments, the instructions comprise a description of administering one or more agents of the disclosure to an individual at risk of the disease or to an individual who is in need of improving basic behavioral functioning, hyperactivity, anxiety, depression, suicidal ideation and/or behavior, sensorimotor gating, pain threshold, memory and/or cognitive functioning.

The instructions relating to the use of composition comprising a compound of Formula (I) to achieve the intended therapeutic effects generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert may indicate that the composition is used for the intended therapeutic utilities. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

Methods of Treatment

Any of the compounds described herein (e.g., a compound of Formula (I)) may be used to treating diseases or disorders. In certain embodiments, provided herein are methods to improve basic behavioral functioning, weight reduction, hyperactivity, anxiety, depression, suicidal ideation and/or behavior, sensorimotor gating, pain threshold, memory, and/or cognitive functioning in a subject in need of the treatment. Such compounds may also be used to treating diseases or disorders associated with DAAO such as a central nervous system disorder (e.g., those described herein). The compounds may also be used to treat an obesity disorder.

As used herein, the term "treating" refers to the application or administration of a composition including one or more active agents to a subject, who is in need of the treatment, for example, having a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To achieve any of the intended therapeutic effects described herein, an effective amount of a compound described herein (e.g., a compound of Formula (I)) may be administered to a subject in need of the treatment via a suitable route.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

A human subject who needs the treatment may be a human patient having, at risk for, or suspected of having a target disease/disorder, such as a CNS disorder, or a disease associated with obesity, e.g., diabetes, hyperglycemia, hypercholesterolemia or hyperlipidemia. A subject having a target disease or disorder can be identified by routine medical examination, e.g., laboratory tests, organ functional tests, and/or behavior tests. A subject suspected of having any of such target disease/disorder might show one or more symptoms of the disease/disorder.

A subject at risk for the disease/disorder can be a subject having one or more of the risk factors for that disease/disorder, for example, a genetic factor. In some instances, the human subject is a child who has, is suspected of having, or is at risk for obesity or a CNS disorder associated with children, for example, attention deficit/hyperactivity disorder (ADHD), autism, Asperger's disorder, obsessive compulsive disorder, depression, suicidal ideation and/or behavior, psychosis, chronic pain, and learning disorder.

The methods and compositions described herein may be used to treat a CNS disorder. Exemplary CNS disorders that can be treated by the methods and compositions described herein include schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

A disease associated with obesity includes diseases and disorders that lead to obesity, as well as diseases and disorders that have a high occurrence rate in obesity patients. Obesity is a medical condition characterized by accumulation of excess body fat to the extent that it may have a negative effect on health. Obesity may be determined by body mass index (BMI), a measurement obtained by dividing a person's weight by the square of the person's height. For example, BMI over 30 kg/m$^2$ may indicate obesity. Exemplary diseases associated with obesity include, but are not limited to, eating disorders, anorexia nervosa, bulimia nervosa, stroke, coronary heart disease, heart attack, congestive heart failure, congenital heart disease, hypertension, diabetes mellitus, hyperlipidemia, hypercholesterolemia, non-alcoholic steatohepatitis, insulin resistance, hyperuricemia, hypothyroidism, osteoarthritis, gallstones, infertility (e.g., hypogonadism and hyperandrogegism), obesity hypoventilation syndrome, obstructive sleep apnea, chronic obstructed pulmonary disease, and asthma.

In some embodiments, the human subject is administered with a compound described herein (e.g., a compound of formula (I)) at a frequency of four times a day to one time every three months, inclusive. In some embodiments, the human subject is administered with a compound described herein (e.g., a compound of formula (I)) at a frequency of four times a day, three doses a day, two doses a day, one dose a day, one dose every other day, one dose every third day, one dose every week, one dose every other week, one dose monthly, one dose every other month, or one time every three months. In some embodiments, the human subject is administered with a compound described herein (e.g., a compound of formula (I)) at a frequency of one time a day, two times a day, three times a day, four times a day, five times a day, six times a day, seven times a day, eight times a day, nine times a day, or ten times a day. In some embodiments, the human subject is administered with a compound described herein (e.g., a compound of formula (I)) at a frequency of four times a day. In some embodiments, the human subject is administered with a compound described herein (e.g., a compound of formula (I)) at a frequency of one time every three months. In some embodiments, the human subject is administered with a compound described herein (e.g., a compound of formula (I)) at a frequency of one time every one month, one time every two months, one time every three months, one time every four months, one time every five months, or one time every six months. In some embodiments, the human subject is treated concurrently with, prior to, or subsequent to, one or more additional pharmaceutical agents for treating and/or reducing the risk for a CNS disorder or a disease associated with obesity.

As used herein, "an effective amount" refers to the amount of each active agent (e.g., the compounds of Formula (I) as described herein) required to confer therapeutic effect on the subject, either alone or in combination with one or more other active agents, such as one or more of the second therapeutic agents described herein. In some embodiment, the therapeutic effect is to inhibit the activity of DAAO (e.g., by at least 20%, 30%, 40%, 50%, 60%, 70%, 80%, 90%, 95%, or higher) in the subject. In some embodiments, the therapeutic effect is improvement of basic behavioral functioning, weight reduction, hyperactivity, anxiety, depression, suicidal ideation and/or behavior, sensorimotor gating, pain threshold, memory, and/or improvement of cognitive functioning. In some embodiments, the therapeutic effect is alleviating one or more symptoms associated with any of the CNS disorders described herein. Alternatively, or in addition, the therapeutic effect is maintaining or reducing body weight of the subject.

Determination of whether an amount of the composition as described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration, genetic factors and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a composition as described herein may be appropriate. Various formulations and devices for achieving sustained release are known in the art.

Generally, for administration of any of the compositions, an exemplary daily dosage might range from about any of 0.1 ag/kg to 3 ag/kg to 30 ag/kg to 300 ag/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering one or more initial doses at a suitable interval over a suitable period. If necessary, multiple maintenance doses can be given to the subject at a suitable interval over a suitable period of time. However, other dosage regimens may be useful, depending on the pattern of pharmacokinetic decay that the practitioner wishes to achieve. For example, dosing from one to four times a day or a week is contemplated. In some embodiments, dosing ranging from about 3 ag/mg to about 2 mg/kg (such as about 3 ag/mg, about 10 ag/mg, about 30 ag/mg, about 100 ag/mg, about 300 ag/mg, about 1 mg/kg, and about 2 mg/kg) may be used. In some embodiments, dosing frequency can be three times a day, twice a day, once a day, once every other day, once every week, once every 2 weeks, once every 4 weeks, once every 2 months, or once every 3 months. The dosing regimen can vary over time.

In some embodiments, for an adult patient of normal weight, doses ranging from about 0.3 to 100 mg/kg/day (e.g., 0.5 to 90 mg/kg/day, 1-50 mg/kg/day, 5-30 mg/kg/day, or 10-20 mg/kg/day) may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a compound described herein will depend on the specific compound described herein, and/or other active ingredient employed, the type and severity of the disease/disorder, whether the composition is administered for preventive or therapeutic purposes, previous therapy, the patient's clinical history and response to the DAAO inhibitor, and the discretion of the attending physician. Typically, the clinician will administer a composition, until a dosage is reached that achieves the desired result.

Conventional methods, known to those of ordinary skill in the art of medicine, can be used to administer the composition (e.g., a pharmaceutical composition, a health food composition, a nutraceutical composition or a medical food composition) to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-week, half (or two week)-, 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water-soluble antibodies can be administered by the drip method, whereby a pharmaceutical formulation containing the compounds of Formula (I) and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the compounds of Formula (I), can be dissolved and administered in a pharmaceutical excipient such as Water-for-Injection, 0.9% saline, or 5% glucose solution.

In one embodiment, a compound described herein is administered via a site-specific or targeted local delivery technique. Examples of site-specific or targeted local delivery techniques include various implantable depot sources of the compound described herein or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Treatment efficacy for a target disease/disorder can be assessed by methods well-known in the art.

Combined Therapy

Also provided herein are combined therapies using any of the compounds described herein and a second therapeutic agent, such as those described herein. The term "combination therapy", as used herein, embraces administration of these agents (e.g., a compound of Formula (I) as described herein and an anti-CNS disorder or anti-obesity agent) in a sequential manner, that is, wherein each therapeutic agent is administered at a different time, as well as administration of these therapeutic agents, or at least two of the agents, in a substantially simultaneous manner. Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., a compound of Formula (I) as described herein) can be administered orally, and a second agent (e.g., an anti-CNS disorder agent or an anti-obesity agent) can be administered intravenously.

As used herein, the term "sequential" means, unless otherwise specified, characterized by a regular sequence or order, e.g., if a dosage regimen includes the administration of a compound described herein and an anti-CNS disorder or anti-obesity agent, a sequential dosage regimen could include administration of the compound described herein before, simultaneously, substantially simultaneously, or after administration of the anti-CNS disorder or anti-obesity agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the agents described herein.

Combination therapy can also embrace the administration of the agents described herein (e.g., a compound of Formula (I) and an anti-CNS disorder or anti-obesity agent) in further combination with other biologically active ingredients (e.g., a different anti-CNS disorder agent) and non-drug therapies (e.g., surgery).

It should be appreciated that any combination of a compound described herein and a second therapeutic agent (e.g., an anti-CNS disorder or anti-obesity agent) may be used in any sequence for treating a target disease. The combinations described herein may be selected on the basis of a number of factors, which include but are not limited to the effectiveness of inhibiting DAAO, improving basic behavioral functioning, weight reduction, hyperactivity, anxiety, depression, suicidal ideation and/or behavior, sensorimotor gating, pain threshold, memory or enhancing cognitive functioning, and/or alleviating at least one symptom associated with the target disease, or the effectiveness for mitigating the side effects of another agent of the combination. For example, a combined therapy described herein may reduce any of the side effects associated with each individual members of the combination, for example, a side effect associated with the second therapeutic agent.

Methods of Preparing Compounds of Formula (I)

The present disclosure provides methods of preparing compounds described herein. In one aspect, the present disclosure provides methods of preparing compounds of Formula (I). In one aspect, provided herein is a method of synthesis (e.g., preparing) of a compound described herein (e.g., a compound of Formula (I)). In some embodiments, provided is a method for preparing the compound of Formula (I), comprising:

(a) providing a compound of formula (Ia)

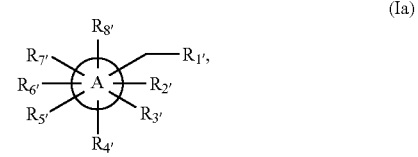

wherein $R_{1'}$, $R_{2'}$, $R_{3'}$, $R_{4'}$, $R_{5'}$, $R_{6'}$, $R_{7'}$, and $R_{8'}$, independently, are each —OH, —NH$_2$ or absent; wherein Ring A is a 5 to 8 membered monocyclic ring system, which optionally comprises at least one heteroatom selected from the group consisting of N, O, P, and S;

(b) reacting the compound of formula (Ia) with 7-(allyloxy)-2,2-diphenylbenzo[d][1,3]dioxole-5-carbonyl chloride, to allow conjugation of the compound of 7-(allyloxy)-2,2-diphenylbenzo[d][1,3]dioxole-5-carbonyl chloride to one or more of $R_{1'}$, $R_{2'}$, $R_{3'}$, $R_{4'}$, $R_{5'}$, $R_{6'}$, $R_{7'}$, and $R_{8'}$ of the compound of formula (Ia), thereby producing a first intermediate; and (c) de-protecting the allyl groups and the cyclic acetal groups in 7-(allyloxy)-2,2-diphenylbenzo[d][1,3]dioxole-5-carbonyl chloride that is conjugated to the compound of Formula (Ia) to obtain the compound of Formula (I).

In some embodiments, Ring A is a 5 to 8 membered monocyclic ring system, which optionally comprises at least one heteroatom selected from the group consisting of N, O, P, and S.

In some embodiments, Ring A is a 5 to 8 membered monocyclic ring system, which comprises at least one N. In some embodiments, Ring A is a 5 to 8 membered monocyclic ring system, which comprises at least one O. In some embodiments, Ring A comprises at least one heteroatom selected from the group consisting of N, O, P, and S. In some embodiments, Ring A is a heterocycle that comprises at least one O. In some embodiments, Ring A is a 5-8 membered heterocycle that comprises at least one O. In some embodiments, Ring A is:

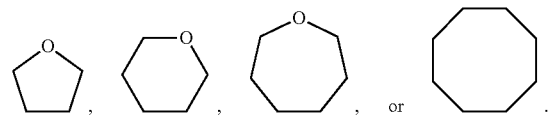

In some embodiments, Ring A is:

In some embodiments, the compound of formula (Ia) is glucose. In some embodiments, the compound of formula (Ia) is glucose in the α form or in β form. In some embodiments, the compound of formula (Ia) is glucose in the α form. In some embodiments, the compound of formula (Ia) is glucose in the β form. In some embodiments, in step (a), a compound of formula (Ia) is

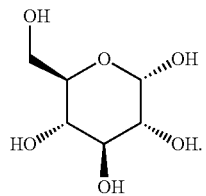

In some embodiments, in step (a), a compound of formula is

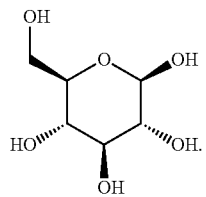 [SMILES: OC[C@H]1O[C@@H](O)[C@H](O)[C@@H](O)[C@@H]1O]

In some embodiments, $R_{1'}$, $R_{2'}$, $R_{3'}$, $R_{4'}$, $R_{5'}$, $R_{6'}$, $R_{7'}$, and $R_{8'}$, independently, are each selected from the group consisting of —OH, —NH$_2$, and absent. In some embodiments, at least one of $R_{1'}$, $R_{2'}$, $R_{3'}$, $R_{4'}$, $R_{5'}$, $R_{6'}$, $R_{7'}$, or $R_{8'}$, is —OH. In some embodiments, all of $R_{1'}$, $R_{2'}$, $R_{3'}$, $R_{4'}$, $R_{5'}$, $R_{6'}$, $R_{7'}$, or $R_{8'}$, are —OH. In some embodiments, at least one of $R_{1'}$, $R_{2'}$, $R_{3'}$, $R_{4'}$, $R_{5'}$, $R_{6'}$, $R_{7'}$, or $R_{8'}$, is —NH$_2$. In some embodiments, at least one of $R_{1'}$, $R_{2'}$, $R_{3'}$, $R_{4'}$, $R_{5'}$, $R_{6'}$, $R_{7'}$, or $R_{8'}$, is absent.

In some embodiments, step (b) comprises reacting the compound of formula (Ia) with

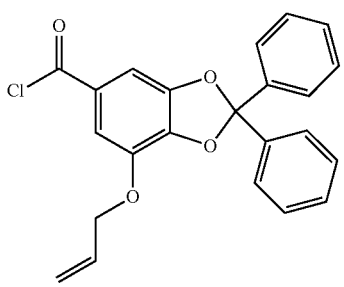 [SMILES: C=CCOc1cc(C(=O)Cl)cc2c1OC(c1ccccc1)(c1ccccc1)O2]

(7-(allyloxy)-2,2-diphenylbenzo[d][1,3]dioxole-5-carbonyl chloride). In some embodiments, step (b) comprises reacting the compound of formula (Ia) with 7-(allyloxy)-2,2-diphenylbenzo[d][1,3]dioxole-5-carbonyl chloride, in presence of a base (e.g., N-methylmorpholine (NMM)), and 4-Dimethylaminopyridine (DMAP). In some embodiments, step (b) comprises reacting the compound of formula (Ia) with 7-(allyloxy)-2,2-diphenylbenzo[d][1,3]dioxole-5-carbonyl chloride, and a base. In some embodiments, the base is trimethylamine (TEA), pyridine, or N-methylmorpholine (NMM).

In some embodiments, step (c) comprises de-protecting the allyl groups and the cyclic acetal groups in 7-(allyloxy)-2,2-diphenylbenzo[d][1,3]dioxole-5-carbonyl chloride that is conjugated to the compound of Formula (Ia) to obtain the compound of formula (I). In some embodiments, step (c) is performed by: step (c1) de-protecting the allyl groups; and step (c2) de-protecting the cyclic acetal groups in 7-(allyloxy)-2,2-diphenylbenzo [d][1,3]dioxole-5-carbonyl chloride that is conjugated to the compound of Formula (Ia). In some embodiments, step (c) is performed by: (c1) de-protecting the allyl groups in 7-(allyloxy)-2,2-diphenylbenzo[d][1,3]dioxole-5-carbonyl chloride that is conjugated to the compound of Formula (Ia). In some embodiments, step (c) is performed by: (c1) de-protecting the allyl groups using palladium catalyst with an amine base. In some embodiments, the amine base is a tertiary amine. In some embodiments, the amine base is a bulky, tertiary amine. In some embodiments, the amine base is t-Butyl amine. In some embodiments, the amine base is an aromatic amine. In some embodiments, step (c) is performed by: (c1) de-protecting the allyl groups, which comprises removing the

(allyl) groups. In some embodiments, step (c) is performed by: (c1) de-protecting the allyl groups using palladium catalyst with aniline. In some embodiments, step (c) is performed by: (c1) de-protecting the allyl groups using Pd(PPh$_3$)$_4$ with aniline.

In some embodiments, step (c) is performed by: (c2) de-protecting the cyclic acetal groups in 7-(allyloxy)-2,2-diphenylbenzo[d][1,3]dioxole-5-carbonyl chloride that is conjugated to the compound of Formula (Ia). In some embodiments, step (c) is performed by: (c2) de-protecting the cyclic acetal groups which comprises converting

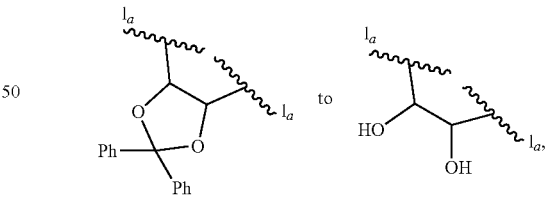

where $1_a$ indicates the attachment of the cyclic acetal to the rest of the cyclic intermediate. In some embodiments, step (c) is performed by: (c2) de-protecting the cyclic acetal groups using palladium catalyst. In some embodiments, step (c) is performed by: (c2) de-protecting the cyclic acetal groups using Pd/C under H$_2$ gas.

In some embodiments, the method for preparing a compound of Formula (I) comprises: prior to step (c2), repeating the process consisting of steps (b) and (c1) for 3-7 times. In some embodiments, the method for preparing the compound of Formula (I) comprises: prior to step (c2), repeating the process consisting of steps (b) and (c1) for 3-4 times, 3-5 times, 3-6 times, 3-7 times, 4-5 times, 4-6 times, 4-7 times, 5-6 times, 5-7 times, or 6-7 times. In some embodiments, the method for preparing the compound of Formula (I) comprises: prior to step (c2), repeating the process consisting of steps (b) and (c1) for 3 times, 4 times, 5 times, 6 times, or 7 times. In some embodiments, the method for preparing the compound of Formula (I) comprises: prior to step (c2), repeating the process consisting of steps (b) and (c1) for 3 times. In some embodiments, the method for preparing the compound of Formula (I) comprises: prior to step (c2), repeating the process consisting of steps (b) and (c1) for 4 times. In some embodiments, the method for preparing the compound of Formula (I) comprises: prior to step (c2), repeating the process consisting of steps (b) and (c1) for 5 times. In some embodiments, the method for preparing the compound of Formula (I) comprises: prior to step (c2), repeating the process consisting of steps (b) and (c1) for 6 times. In some embodiments, the method for preparing the compound of Formula (I) comprises: prior to step (c2), repeating the process consisting of steps (b) and (c1) for 7 times.

In some embodiments, the method for preparing the compound of Formula (I) comprises: prior to step (c2), repeating the process consisting of steps (b) and (c1) for 3-7 times.

In some embodiments, the method for preparing the compound of Formula (I) further comprising purifying the compound of Formula (I) produced after step (c). In some embodiments, the method for preparing the compound of Formula (I) further comprising purifying the intermediate produced after step (c). In some embodiments, the purifying comprises one or more purification procedures. In some embodiments, the purifying comprises re-crystallization and chromatography (e.g., flash column chromatography) or a combination thereof. In some embodiments, the purifying comprises re-crystallization. In some embodiments, the purifying comprises chromatography.

The present disclosure provides methods of synthesizing compounds described herein. In view of the Examples and disclosure provided herein, one of ordinary skill in the art would understand synthetic techniques to synthesize the compounds described herein. One of ordinary skill in the art would recognize the synthetic techniques (e.g., standard organic synthetic reactions) to synthesize the compounds described herein based on the Examples and disclosure provided herein.

General Techniques

The practice of the present invention will employ, unless otherwise indicated, conventional techniques of neuroscience, molecular biology (including recombinant techniques), microbiology, cell biology, biochemistry and immunology, which are within the skill of the art. Such techniques are explained fully in the literature, such as, Current protocol in Neuroscience (Developmental Editor: Eric Prager, Online ISBN: 9780471142300, DOI: 10.1002/0471142301). Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The specific embodiments provided herein are, therefore, to be construed as merely illustrative, and not limitative of the remainder of the disclosure in any way whatsoever. All publications cited herein are incorporated by reference for the purposes or subject matter referenced herein.

EXAMPLES

Example 1. Synthesis of 7-(allyloxy)-2,2-diphenyl-benzo[d][1,3]dioxole-5-carbonyl chloride (5)

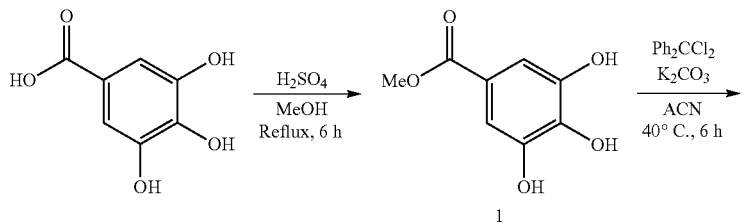

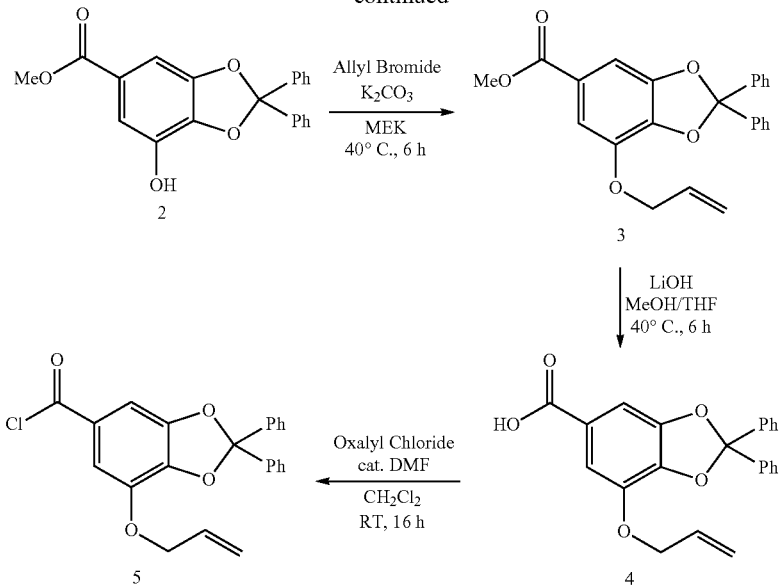

Preparation of methyl 3,4,5-trihydroxybenzoate (1)

To a solution of 3,4,5-trihydroxybenzoic acid (10.0 g, 58.8 mmol) in methanol (118.0 mL) at RT was added sulfuric acid (3.1 mL, 58.8 mmol). The resulting mixture was heated to reflux for 6 hrs. After the reaction was complete, the reaction mixture was concentrated under vacuum. The residue was diluted with ethyl acetate, extracted with water, washed with brine, dried over anhydrous magnesium sulfate and filtered. The filtrate was concentrated in vacuo to afford methyl 3,4,5-trihydroxybenzoate (1) as a white solid (9.6 g, 89%). $^1$H NMR (MeOD, 400 MHz) δ 7.03 (s, 2H), 3.81 (s, 3H).

Preparation of methyl 7-hydroxy-2,2-diphenylbenzo[d][1,3]dioxole-5-carboxylate (2)

To a solution of 3,4,5-trihydroxybenzoate (1, 10.0 g, 54.3 mmol) in acetonitrile (543.0 mL) was added potassium carbonate (15.0 g, 108.6 mmol) and α,α-dichlorodiphenylmethane (9.9 mL, 51.6 mmol). The mixture was stirred at 40° C. for 6 hrs. After the reaction was complete, the mixture was concentrated under vacuum. The residue was diluted with dichloromethane, extracted with water, washed with brine, dried over anhydrous magnesium sulfate and filtered. The filtrate was concentrated in vacuo. The resulting residue was purified by flash column chromatography with silica gel and ethyl acetate/hexanes (1:3) to afford methyl 7-hydroxy-2,2-diphenylbenzo[d][1,3]dioxole-5-carboxylate (2) as a white solid (10.5 g, 55%). $^1$H NMR (CDCl$_3$, 400 MHz) δ 7.57-7.55 (m, 4H), 7.39-7.34 (m, 7H), 7.20 (s, 1H), 3.84 (s, 3H).

Preparation of methyl 7-(allyloxy)-2,2-diphenyl-benzo[d][1,3]dioxole-5-carboxylate (3)

To a solution of methyl 7-hydroxy-2,2-diphenylbenzo[d][1,3]dioxole-5-carboxylate (2, 10.0 g, 28.7 mmol) in methyl ethyl ketone (144.0 mL) was added potassium carbonate (7.9 g, 57.4 mmol) and allyl bromide (8.7 mL, 100.5 mmol). The mixture was stirred at 40° C. for 6 hrs. After the reaction was complete, the mixture was concentrated in vacuo. The residue was diluted with dichloromethane, extracted with water, washed with brine, dried over anhydrous magnesium sulfate and filtered. The filtrate was stripped down in vacuo. The residue was purified by flash column chromatography with silica gel and ethyl acetate/hexanes (1:4) to afford Methyl 7-(allyloxy)-2,2-diphenylbenzo[d][1,3]dioxole-5-carboxylate (3) as a white solid (10.4 g, 93%). $^1$H NMR (CDCl$_3$, 400 MHz) δ 7.59-7.57 (m, 4H), 7.37 (d, J=5.2 Hz, 6H), 7.32 (s, 1H), 7.26 (s, 1H), 6.09-6.02 (m, 1H), 5.40 (d, J=17.2 Hz, 1H), 5.28 (d, J=10.5 Hz, 1H), 4.70 (d, J=5.4 Hz, 2H), 3.85 (s, 3H).

Preparation of 7-(allyloxy)-2,2-diphenylbenzo[d][1,3]dioxole-5-carboxylic acid (4)

To a solution of methyl 7-(allyloxy)-2,2-diphenylbenzo[d][1,3]dioxole-5-carboxylate (3, 10.0 g, 28.7 mmol) in methanol/tetrahydrofuran (1:1, 102.0 mL) was added lithium hydroxide (1.2 g, 51.5 mmol). The resulting mixture was stirred at 40° C. for 6 hrs. The mixture was concentrated under vacuum. The resulting residue was made acidic (pH=5) with the dropwise addition of 10% HCl$_{(aq)}$. The solid was collected and purified by recrystallization with ethyl acetate/hexanes (1:4) to afford 7-(allyloxy)-2,2-diphenylbenzo[d][1,3]dioxole-5-carboxylic acid (4) as a white solid (9.0 g, 93%). $^1$H NMR (CDCl$_3$, 400 MHz) δ 7.60-7.58 (m, 4H), 7.38-7.37 (m, 7H), 7.32 (s, 1H), 6.11-6.01 (m, 1H), 5.41 (d, J=17.2 Hz, 1H), 5.29 (d, J=10.8 Hz, 1H), 4.71 (d, J=5.2 Hz, 2H).

Preparation of 7-(allyloxy)-2,2-diphenylbenzo[d][1,3]dioxole-5-carbonyl chloride (5)

To a stirring solution of 7-(allyloxy)-2,2-diphenylbenzo[d][1,3]dioxole-5-carboxylic acid (4) (9.0 g, 24.0 mmol) in dichloromethane (120.0 mL) was added oxalyl chloride (6.2 mL, 72.1 mmol) and DMF (0.1 mL) at 0° C. The mixture was stirred at RT for 12 hrs. The mixture was concentrated under vacuum to afford 7-(allyloxy)-2,2-diphenylbenzo[d][1,3]dioxole-5-carbonyl chloride (5) (9.1 g, crude) as a yellow solid. $^1$H NMR (CDCl$_3$, 400 MHz) δ 7.59-7.58 (m, 4H), 7.42-7.39 (m, 8H), 6.11-6.01 (m, 1H), 5.44 (dd, J=17.2, 1.2 Hz, 1H), 5.33 (dd, J=10.4, 0.9 Hz, 1H), 4.73 (d, J=5.4 Hz, 2H).

Example 2. Synthesis of α form of (2R,3R,4S,5R, 6R)-6-(((3,4-dihydroxy-5-((3,4,5-trihydroxybenzoyl) oxy)benzoyl)oxy)methyl)tetrahydro-2H-pyran-2,3,4, 5-tetrayl tetrakis(3,4-dihydroxy-5-((3,4,5-trihydroxybenzoyl)oxy)benzoate) (10)
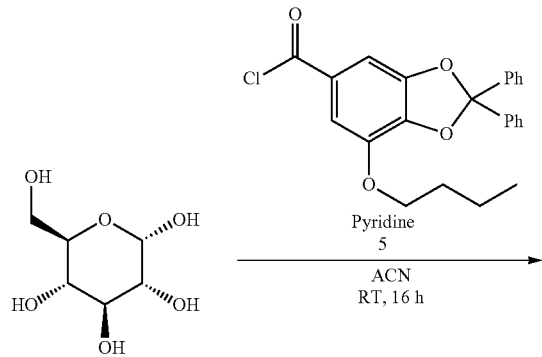
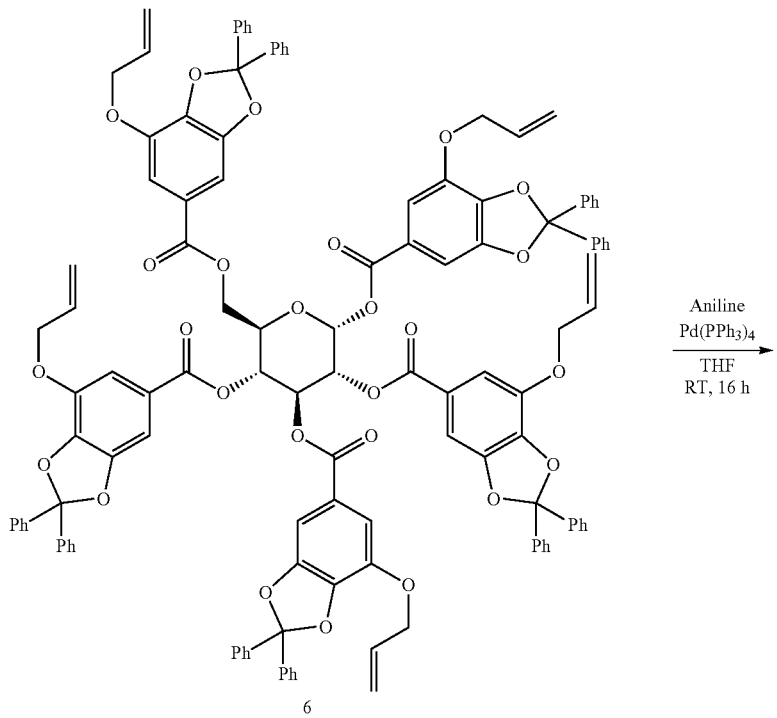

-continued
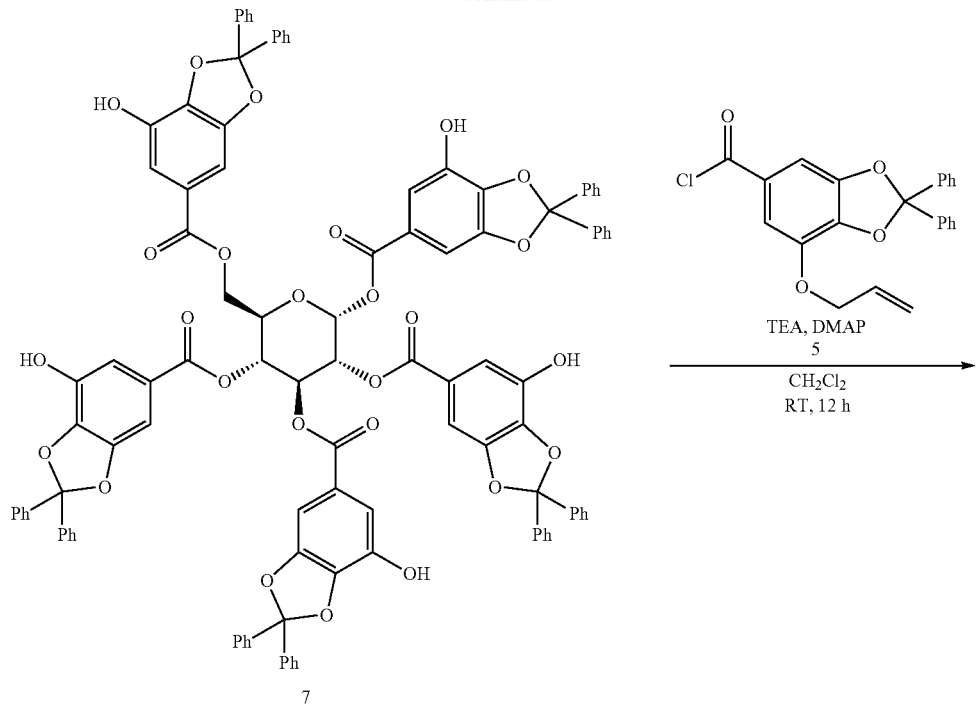
7
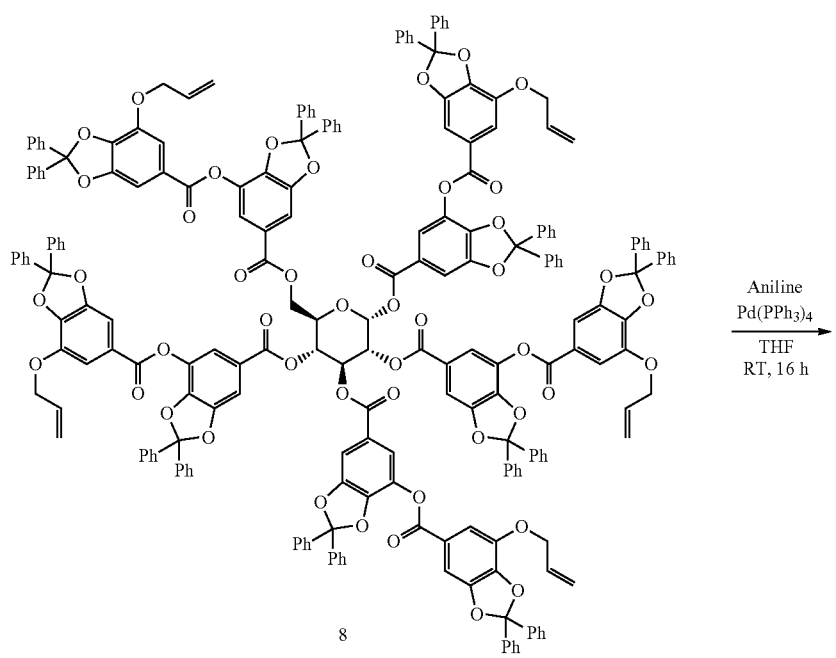
8

-continued
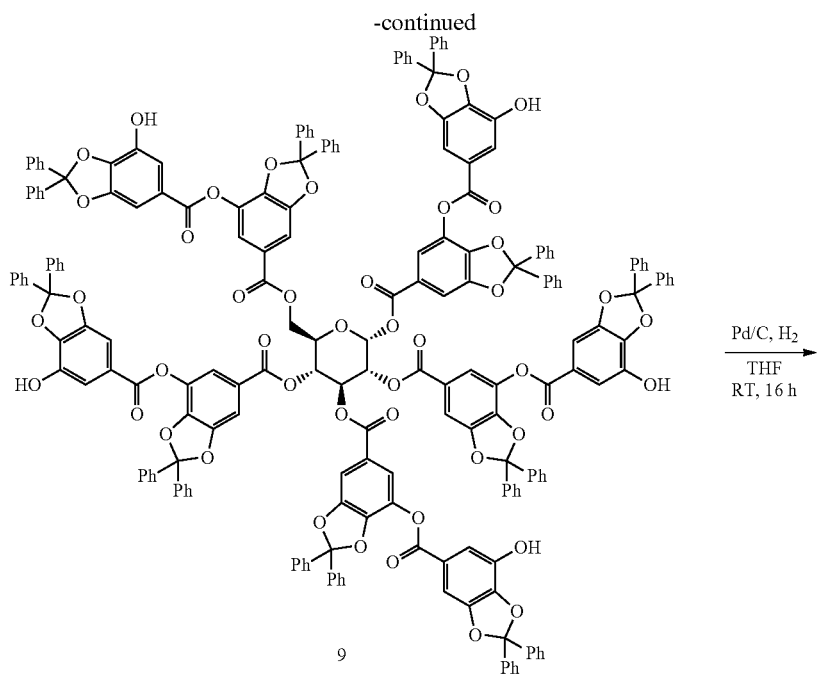
9
Pd/C, H₂
―――――→
THF
RT, 16 h
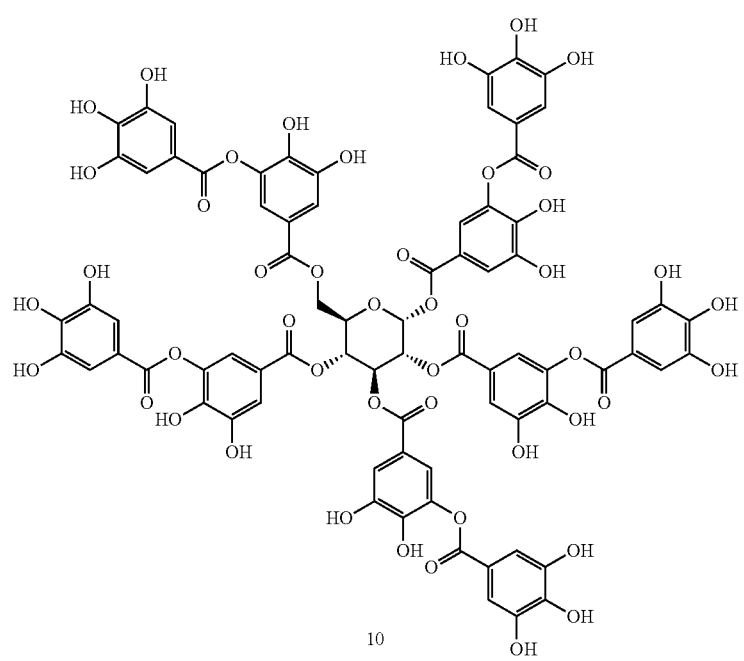 [SMILES: O=C(OC[C@H]1O[C@H](OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1]
10

Preparation of α form of (2R,3R,4S,5R,6R)-6-(((7-(allyloxy)-2,2-diphenylbenzo[d][1,3]dioxole-5-carbonyl)oxy)methyl)tetrahydro-2H-pyran-2,3,4,5-tetrayl tetrakis(7-(allyloxy)-2,2-diphenyl benzo[d][1,3]dioxole-5-carboxylate) (6)

A mixture of a-D-(+)-glucose (1.5 g, 8.3 mmol), pyridine (9.4 mL, 116.6 mmol) and 7-(allyloxy)-2,2-diphenylbenzo[d][1,3]dioxole-5-carbonyl chloride (5) (28.9 g, 58.3 mmol) in anhydrous acetonitrile (43.0 mL) was stirred at RT for 16 hrs. After the reaction was complete, the mixture was evaporated in vacuo. The residue was diluted with dichloromethane, extracted with water, washed with brine, dried over anhydrous magnesium sulfate and filtered. The filtrate was concentrated in vacuo. The residue was purified by flash column chromatography with silica gel and ethyl acetate/hexanes (1:3) to afford the compound (6) (10.2 g, 62%) as a white solid. $^1$H NMR (CDCl$_3$, 600 MHz) δ 7.62-7.58 (m, 8H), 7.55-7.47 (m, 12H), 7.40-7.29 (m, 34H), 7.21 (s, 1H), 7.19 (s, 1H), 7.16 (s, 1H), 7.14 (s, 1H), 7.11 (s, 2H), 6.70 (d, J=3.7 Hz, 1H), 6.10 (t, J=10.0 Hz, 1H), 6.07-5.92 (m, 4H), 5.88-5.81 (m, 1H), 5.67 (t, J=10.0 Hz, 1H), 5.46 (dd, J=10.3, 3.7 Hz, 1H), 5.43 (s, 1H), 5.40 (s, 1H), 5.37-5.31 (m, 2H), 5.27-5.17 (m, 5H), 5.10 (d, J=10.6 Hz, 1H), 4.71-4.69 (m, 4H), 4.62 (d, J=5.5 Hz, 2H), 4.57-4.54 (m, 3H), 4.46-4.44 (m, 3H), 4.29 (dd, J=12.5, 4.6 Hz, 1H).

Preparation of α form of (2R,3R,4S,5R,6R)-6-(((7-hydroxy-2,2-diphenylbenzo[d][1,3]dioxole-5-carbonyl)oxy)methyl)tetrahydro-2H-pyran-2,3,4,5-tetrayl tetrakis(7-hydroxy-2,2-diphenyl benzo[d][1,3]dioxole-5-carboxylate) (7)

To a solution of the compound (6) (10.0 g, 5.1 mmol) in anhydrous tetrahydrofuran (51.0 mL) was added aniline (1.9 mL, 20.4 mmol) and tetrakis(triphenylphosphine)palladium (3.0 g, 2.6 mmol). The mixture was stirred at RT for 16 hrs. The mixture was filtered through Celite and the filtrate was concentrated in vacuo. The residue was purified by flash column chromatography with silica gel and ethyl acetate/hexanes (1:1) to afford the compound (7) (7.4 g, 82%) as a white solid. $^1$H NMR (CDCl$_3$, 600 MHz) δ 7.55-6.97 (m, 60H), 6.59 (d, J=3.4 Hz, 1H), 6.07 (t, J=10.0 Hz, 1H), 5.69 (t, J=10.0 Hz, 1H), 5.42 (dd, J=10.1, 3.5 Hz, 1H), 4.53 (d, J=11.0 Hz, 1H), 4.42-4.40 (m, 1H), 4.25 (dd, J=12.4, 4.4 Hz, 1H).

Preparation of α form of (2R,3R,4S,5R,6R)-2-((7-((7-(allyloxy)-2,2-diphenylbenzo [d][1,3]dioxole-5-carbonyl)oxy)-2,2-diphenylbenzo[d][1,3]dioxole-5-carbonyl)oxy)-6-(((7-((7-(allyloxy)-2,2-diphenylbenzo[d][1,3]dioxole-5-carbonyl)oxy)-2,2-diphenylbenzo[d][1,3]dioxole-5-carbonyl)oxy) methyl)tetrahydro-2H-pyran-3,4,5-triyltris(7-((7-(allyloxy)-2,2-diphenylbenzo[d][1,3]dioxole-5-carbonyl)oxy)-2,2-diphenylbenzo[d][1,3]dioxole-5-carboxylate) (8)

A mixture of the compound (7) (7.4 g, 4.2 mmol), triethylamine (17.6 mL, 126.2 mmol), 4-dimethylamino pyridine (0.3 g, 2.1 mmol) and the compound (5) (16.5 g, 42.1 mmol) in dichloromethane (84.0 mL) was stirred at RT for 12 hrs. After the reaction was complete, the mixture was extracted with water, washed with brine, dried over anhydrous magnesium sulfate and filtered. The filtrate was evaporated in vacuo. The residue was purified by flash column chromatography with silica gel and ethyl acetate/hexanes (1:2) to afford the compound (8) (12.7 g, 85%) as a white solid. $^1$H NMR (CDCl$_3$, 400 MHz) δ 7.61-7.28 (m, 120H), 6.76 (d, J=4.0 Hz, 1H), 6.12 (t, J=10.0 Hz, 1H), 6.08-5.96 (m, 5H), 5.68 (t, J=10.0 Hz, 1H), 5.51 (dd, J=10.0, 3.2 Hz, 1H), 5.43-5.35 (m, 5H), 5.29-5.23 (m, 5H), 4.72-4.64 (m, 10H), 4.47 (d, J=10.8 Hz, 2H), 4.42-4.38 (m, 1H).

Preparation of α form of (2R,3R,4S,5R,6R)-6-(((7-((7-hydroxy-2,2-diphenylbenzo[d][1,3]dioxole-5-carbonyl)oxy)-2,2-diphenylbenzo[d][1,3]dioxole-5-carbonyl)oxy)methyl) tetrahydro-2H-pyran-2,3,4,5-tetrayltetrakis(7-((7-hydroxy-2,2-diphenylbenzo[d][1,3]dioxole-5-carbonyl)oxy)-2,2-diphenylbenzo[d][1,3]dioxole-5-carboxylate) (9)

A mixture of the compound (8) (12.7 g, 3.6 mmol), aniline (1.3 mL, 14.3 mmol), tetrakis(triphenylphosphine)palladium (2.1 g, 1.8 mmol) in anhydrous tetrahydrofuran (70.0 mL) was stirred at RT for 16 hrs. The mixture was filtered through a bed of Celite and the filtrate was concentrated in vacuo. The crude product was purified by flash column chromatography with silica gel and ethyl acetate/hexanes (1:1) to afford the compound (9) (10.7 g, 89%) as a white solid. $^1$H NMR (CDCl$_3$, 400 MHz) δ 7.59-7.12 (m, 120H), 6.74 (d, J=3.3 Hz, 1H), 6.08 (t, J=9.6 Hz, 1H), 5.59-5.52 (m, 2H), 4.59-4.56 (m, 1H), 4.52-4.50 (m, 1H), 4.39-4.37 (m, 1H).

Preparation of α form of (2R,3R,4S,5R,6R)-6-(((3,4-dihydroxy-5-((3,4,5-trihydroxybenzoyl)oxy)benzoyl)oxy)methyl)tetrahydro-2H-pyran-2,3,4,5-tetrayltetrakis(3,4-dihydroxy-5-((3,4,5-trihydroxybenzoyl)oxy)benzoate) (10)

To a stirred solution of the compound (9) (100.0 mg, 0.02 mmol) in anhydrous tetrahydrofuran (3.0 mL) was added 10 wt % Pd/C (100 mg). The mixture was stirred at RT under H$_2$ (8 atm) for 24 hrs. The mixture was then filtered through Celite and washed with acetone (10 mL), and the combined filtrates were evaporated in vacuo. The residue was precipitated with ethyl acetate/hexanes (1:25) to give the compound (10) as an off-white solid (37.0 mg, 64%). $^1$H NMR (MeOD, 400 MHz) δ 7.59-6.96 (m, 20H), 6.80 (s, 1H), 6.19 (t, J=9.6 Hz, 1H), 5.79 (t, J=9.2 Hz, 1H), 5.62-5.61 (m, 1H), 4.68 (s, 1H), 4.52 (s, 2H). ESI-MS, m/z 1699 [M-H]$^-$.

Example 3. Synthesis of α form of (2R,3R,4S,5R, 6R)-6-(((3-((3,4-dihydroxy-5-((3,4,5-trihydroxybenzoyl)oxy)benzoyl)oxy)-4,5-dihydroxybenzoyl)oxy)methyl)tetrahydro-2H-pyran-2,3,4,5-tetrayltetrakis (3-((3,4-dihydroxy-5-((3,4,5-trihydroxybenzoyl)oxy)benzoyl)oxy)-4,5-dihydroxybenzoate) (13)
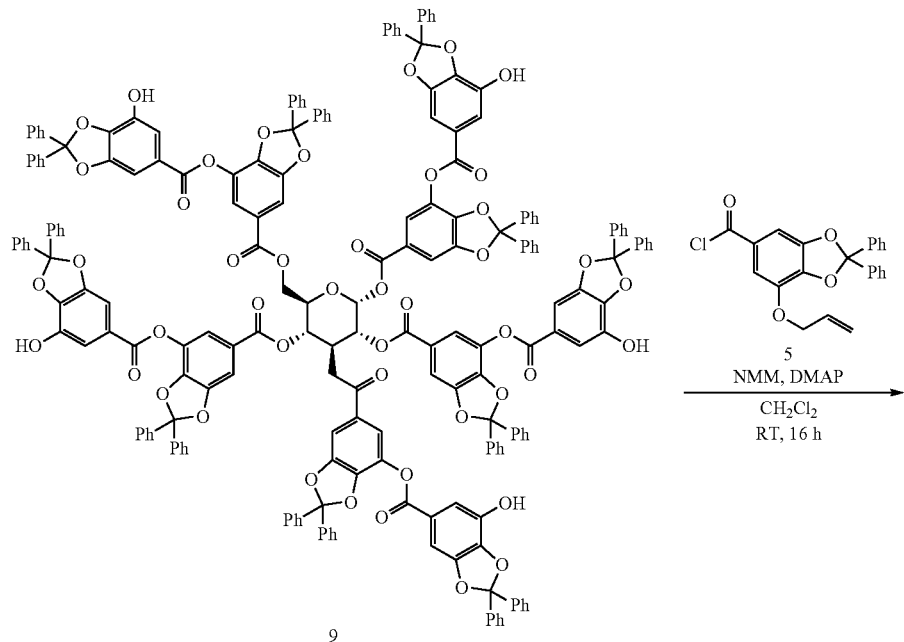
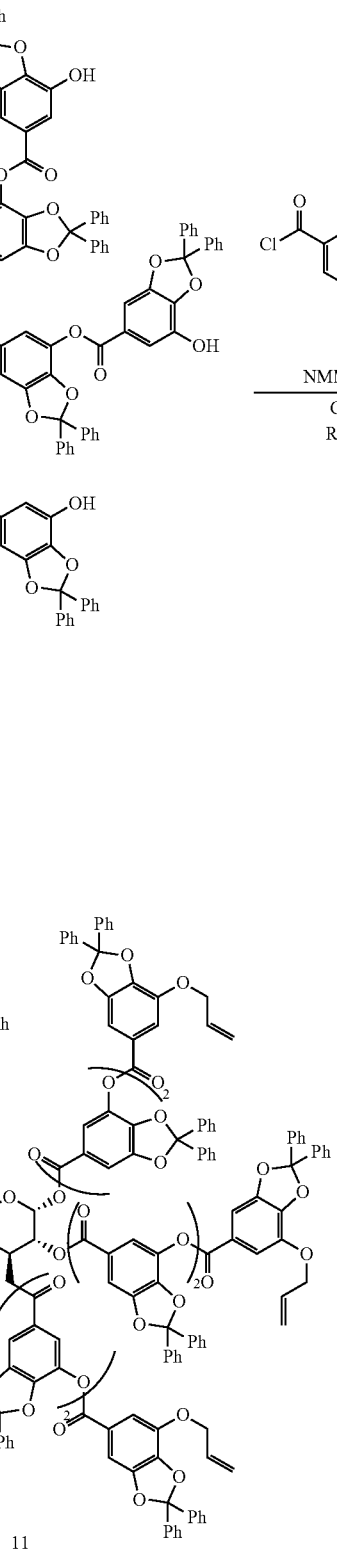

-continued
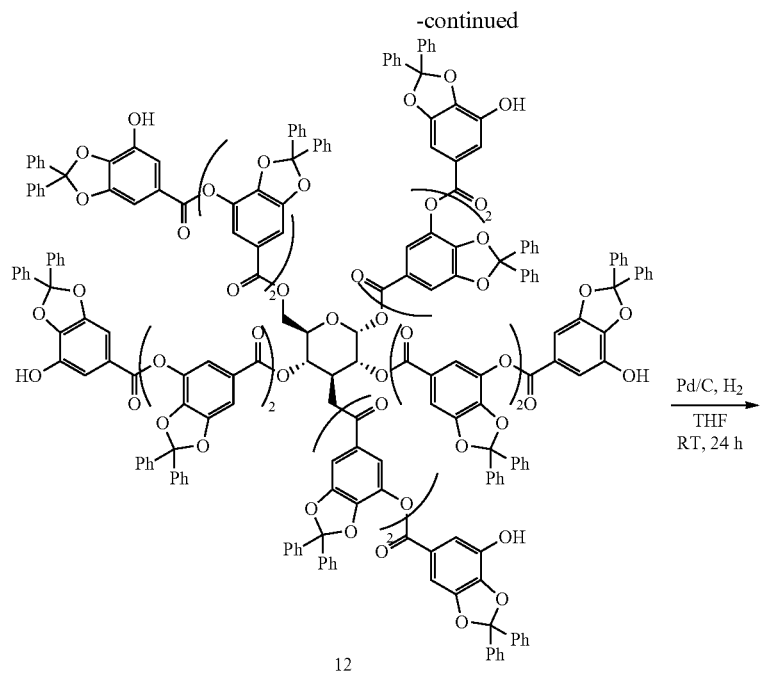
12
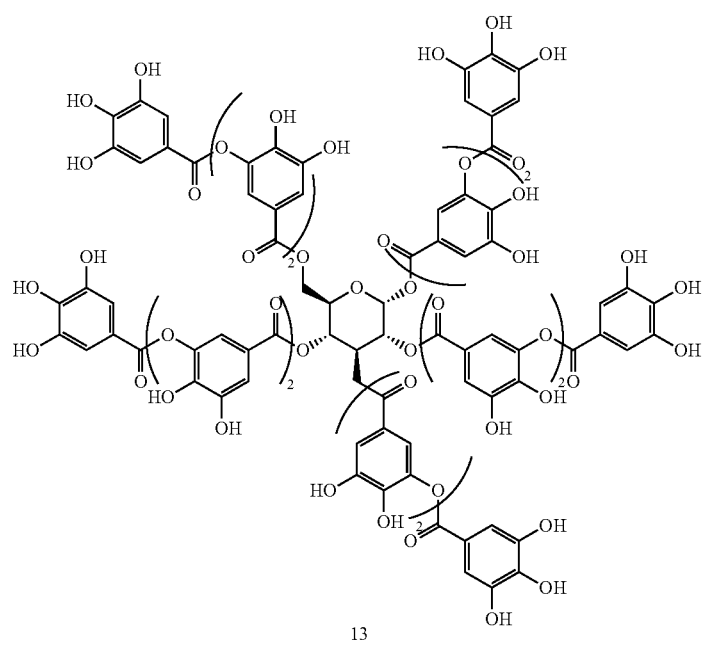
13

Preparation of α form of (2R,3R,4S,5R,6R)-6-((7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydro-2H-pyran-3,4,5-tetrayl tetrakis(7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (11)

A mixture of the compound (9) (10.7 g, 3.2 mmol), N-methylmorpholine (10.6 mL, 96.0 mmol), 4-dimethylaminopyridine (0.2 g, 1.6 mmol) and the compound (5) (12.6 g, 32.0 mmol) in mixture was extracted with water, washed with brine, dried over anhydrous magnesium sulfate and filtered. The filtrate was evaporated in vacuo. The residue was purified by flash column chromatography with silica gel and ethyl acetate/hexanes (1:2) to afford the compound (11) (15.0 g, 91%) as a white solid. $^1$H NMR (CDCl$_3$, 400 MHz) δ 7.66-7.26 (m, 180H), 6.79 (d, J=3.2 Hz, 1H), 6.16 (t, J=9.8 Hz, 1H), 6.13-6.02 (m, 5H), 5.71 (t, J=10.0 Hz, 1H), 5.55 (dd, J=10.4, 3.4 Hz, 1H), 5.47-5.40 (m, 5H), 5.33-5.28 (m, 5H), 4.77-4.64 (m, 10H), 4.52-4.49 (m, 2H), 4.43-4.41 (m, 1H).

Preparation of α form of (2R,3R,4S,5R,6R)-6-(((7-((7-((7-hydroxy-2,2-diphenylbenzo [d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydro-2H-pyran-2,3,4,5-tetrayl tetrakis(7-((7-((7-hydroxy-2,2-diphenylbenzo [d][1,3]dioxole-5-carbonyl)oxy)-2,2-diphenylbenzo [d][1,3]dioxole-5-carbonyl)oxy)-2,2-diphenylbenzo [d][1,3]dioxole-5-carboxylate) (12)

To a stirred solution of the compound (11) (15.0 g, 3.6 mmol) in anhydrous tetrahydrofuran (60.0 mL) was added aniline (1.1 mL, 11.7 mmol) and tetrakis(triphenyl phosphine)palladium (1.7 g, 1.5 mmol). The mixture was stirred at RT under N$_2$ for 24 hrs. The mixture was filtered through a bed of Celite and the filtrate was concentrated in vacuo. The residue was purified by flash column chromatography with silica gel and ethyl acetate/hexanes (1:1) to afford the compound (12) (12.3 g, 85%) as a white solid. $^1$H NMR (CDCl$_3$, 400 MHz) δ 7.58-7.22 (m, 180H), 6.73 (d, J=3.5 Hz, 1H), 6.09 (t, J=9.2 Hz, 1H), 5.62 (t, J=9.2 Hz, 1H), 5.51 (dd, J=9.7, 2.9 Hz, 1H), 4.48-4.46 (m, 2H), 4.39-4.37 (m, 1H).

Preparation of α form of (2R,3R,4S,5R,6R)-6-(((3-((3,4-dihydroxy-5-((3,4,5-trihydroxybenzoyl)oxy)benzoyl)oxy)-4,5-dihydroxybenzoyl)oxy)methyl)tetrahydro-2H-pyran-2,3,4,5-tetrayl tetrakis(3-((3,4-dihydroxy-5-((3,4,5-trihydroxybenzoyl)oxy)benzoyl)oxy)-4,5-dihydroxybenzoate) (13)

To a stirred solution of the compound (12) (100.0 mg, 0.02 mmol) in anhydrous tetrahydrofuran (3.0 mL) was added 10 wt % Pd/C (100 mg). The mixture was stirred at RT under H$_2$ (8 atm) for 24 hrs. The mixture was then filtered through Celite, washed with acetone (10 mL) and the combined filtrates were evaporated in vacuo. The residue was precipitated with ethyl acetate/hexanes (1:25) to give the compound (13) as an off-white solid (37.0 mg, 64%). $^1$H NMR (MeOD, 400 MHz) δ 7.59-7.12 (m, 30H), 6.81 (d, J=9.2 Hz, 1H), 6.19 (s, 1H), 5.80 (s, 1H), 5.62 (s, 1H), 4.69 (s, 1H), 4.53 (s, 2H). ESI-MS, m/z 1229 [M-2H]$^{2-}$.

Example 4. Synthesis of α form of (2R,3R,4S,5R,6R)-6-(((3-((3-((3,4-dihydroxy-5-((3,4,5-trihydroxybenzoyl)oxy)benzoyl)oxy)-4,5-dihydroxybenzoyl)oxy)-4,5-dihydroxybenz oyl)oxy)methyl)tetrahydro-2H-pyran-2,3,4,5-tetrayltetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenz oate) (16)

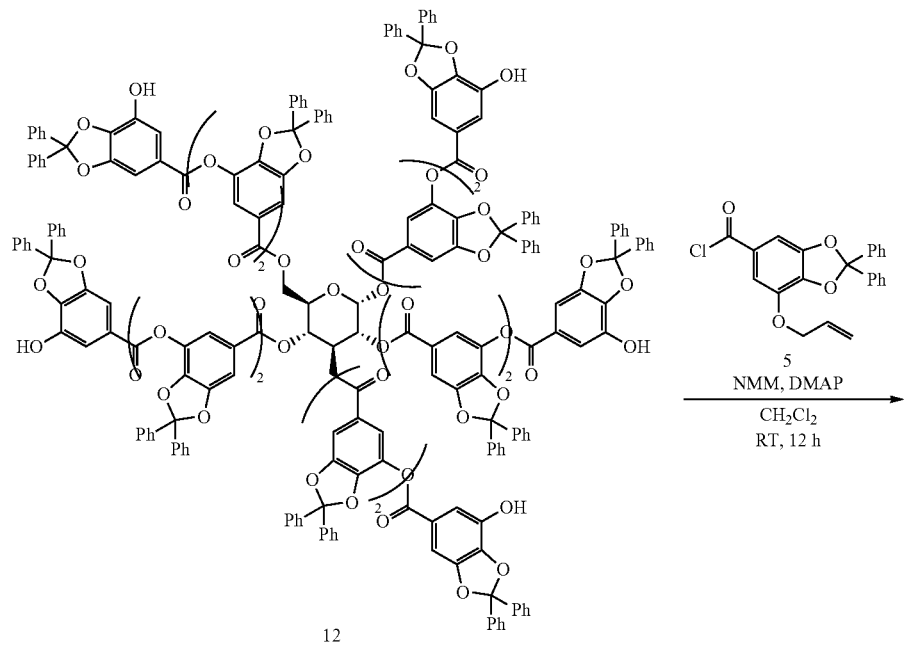

12

-continued
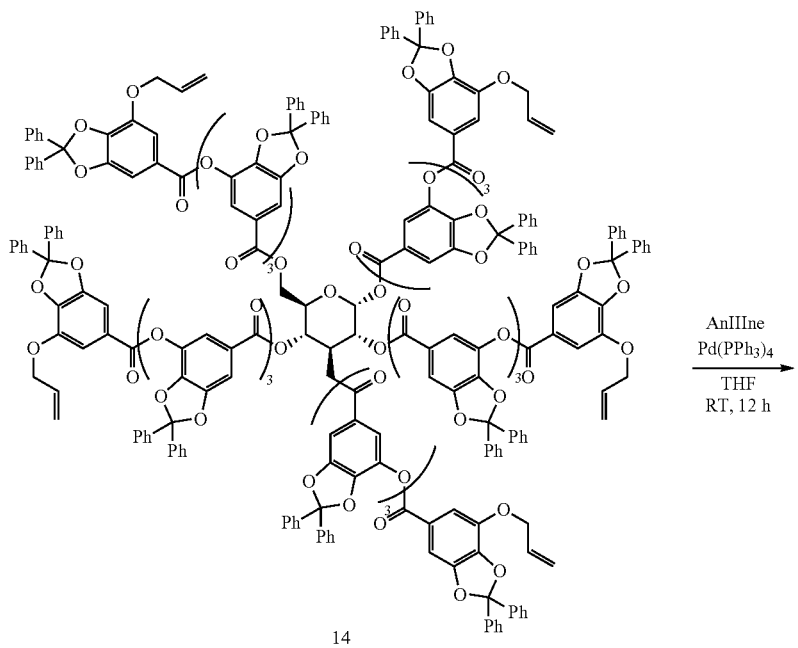
14
$\xrightarrow{\text{Aniline} \atop \text{Pd(PPh}_3)_4}$ THF RT, 12 h
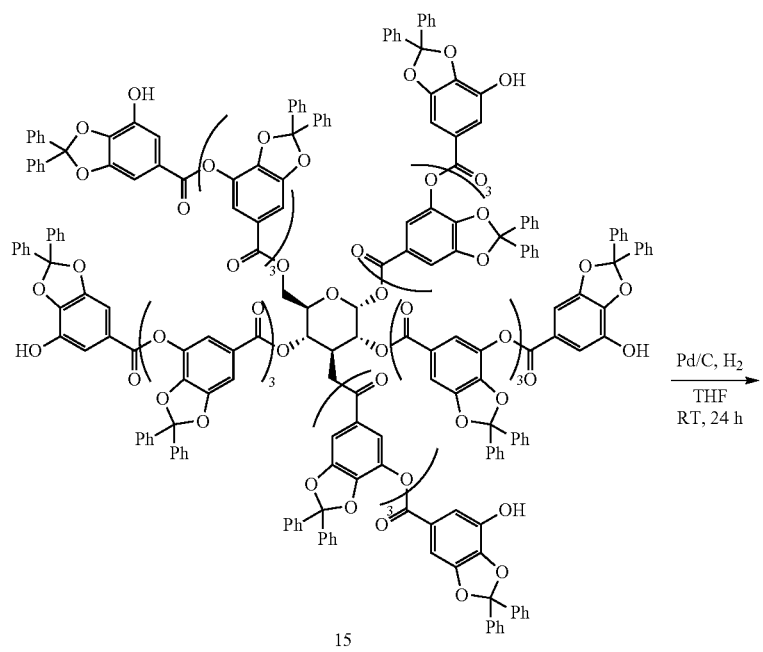
15
$\xrightarrow{\text{Pd/C, H}_2}$ THF RT, 24 h -continued

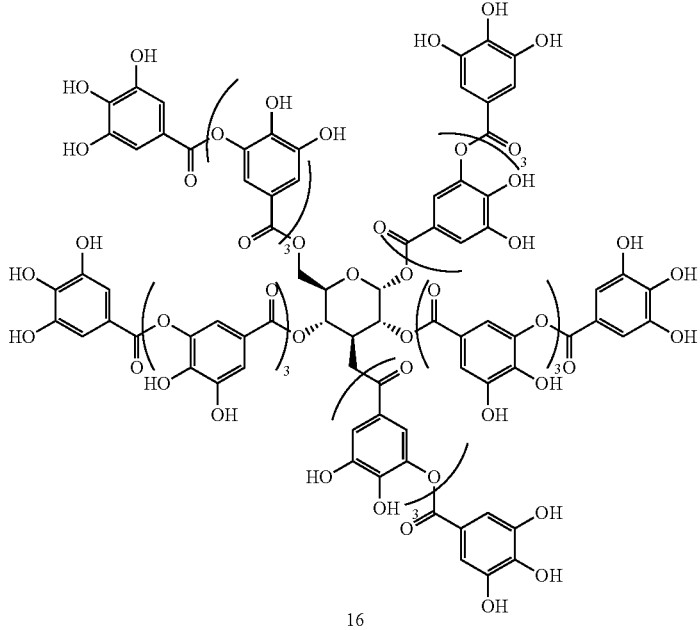

16

Preparation of α form of (2R,3R,4S,5R,6R)-6-((7-((7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydro-2H-pyran-2,3,4,5-tetrayl tetrakis(7-((7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (14)

To a stirred solution of the compound (12) (2.0 g, 0.4 mmol) in dichloromethane (8.0 mL) was added N-methylmorpholine (10.6 mL, 96.0 mmol), 4-dimethylaminopyridine (25.0 mg, 0.2 mmol) and the compound (5) (1.6 g, 4.1 mmol). The mixture was stirred at RT for 12 hrs. After the reaction was complete, the mixture was extracted with water, washed with brine, dried over anhydrous magnesium sulfate and filtered. The filtrate was evaporated in vacuo. The residue was purified by flash column chromatography with silica gel and ethyl acetate/hexanes (1:2) to afford the compound (14) (2.5 g, 92%) as white solid. $^1$H NMR (CDCl$_3$, 600 MHz) δ 7.65-7.24 (m, 240H), 6.75 (d, J=3.6 Hz, 1H), 6.12 (t, J=9.6 Hz, 1H), 6.10-6.00 (m, 5H), 5.67 (t, J=9.6 Hz, 1H), 5.51 (dd, J=10.2, 3.6 Hz, 1H), 5.44-5.38 (m, 5H), 5.32-5.26 (m, 5H), 4.72-4.64 (m, 10H), 4.49-4.47 (m, 2H), 4.38-4.36 (m, 1H).

Preparation of α form of (2R,3R,4S,5R,6R)-6-(((7-((7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydro-2H-pyran-2,3,4,5-tetrayltetrakis(7-((7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (15)

To a stirred solution of the compound (14) (2.5 g, 0.4 mmol) in dry tetrahydrofuran (8.0 mL) was added aniline (0.2 mL, 1.5 mmol) and tetrakis(triphenyl phosphine)palladium (0.2 g, 0.2 mmol). The mixture was stirred at RT for 12 hrs. The mixture was filtered through Celite and the filtrate was concentrated in vacuo. The residue was purified by flash column chromatography with silica gel and ethyl acetate/hexanes (1:1) to afford the compound (15) (2.3 g, 93%) as white solid. $^1$H NMR (CDCl$_3$, 600 MHz) δ 7.59-7.12 (m, 240H), 6.72 (d, J=3.7 Hz, 1H), 6.09 (t, J=10.8 Hz, 1H), 5.64 (t, J=10.0 Hz, 1H), 5.47 (dd, J=10.7 Hz, 3.7 Hz, 1H), 4.45-4.44 (m, 2H), 4.36-4.35 (m, 1H).

Preparation of α form of (2R,3R,4S,5R,6R)-6-(((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy) methyl)tetrahydro-2H-pyran-2,3,4,5-tetrayl tetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (16)

To a stirred solution of the compound (15) (100.0 mg, 0.02 mmol) in anhydrous tetrahydrofuran (3.0 mL) was added 10 wt % Pd/C (100 mg). The mixture was stirred at RT under H$_2$ (8 atm) for 24 hrs. The mixture was then filtered through Celite, washed with acetone (10 mL) and the combined filtrates were evaporated in vacuo. The residue was precipitated with ethyl acetate/hexanes (1:25) to give the compound (16) as an off-white solid (21.5 mg, 43%). $^1$H NMR (MeOD, 600 MHz) δ 7.60-7.03 (m, 40H), 6.82 (d, J=11.4 Hz, 1H), 6.20 (s, 1H), 5.81 (s, 1H), 5.68-5.63 (m, 1H), 4.70 (s, 2H), 4.54 (s, 1H). ESI-MS, m/z 1609 [M−2H]$^{2-}$.

Example 5. Synthesis of β form of (2S,3R,4S,5R, 6R)-6-(((3-((3,4-dihydroxy-5-((3,4,5-trihydroxybenzoyl)oxy)benzoyl)oxy)-4,5-dihydroxybenzoyl)oxy) methyl)tetrahydro-2H-pyran-2,3,4,5-tetrayltetrakis (3-((3,4-dihydroxy-5-((3,4,5-trihydroxybenzoyl)oxy) benzoyl) oxy)-4,5-dihydroxybenzoate) (23)

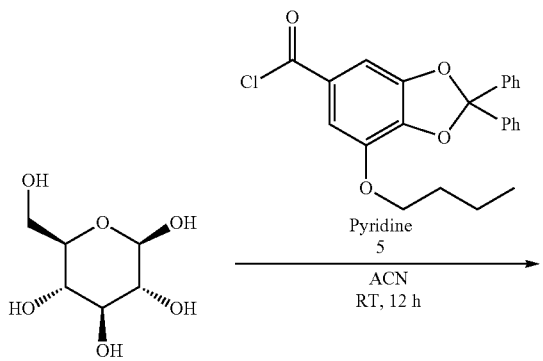

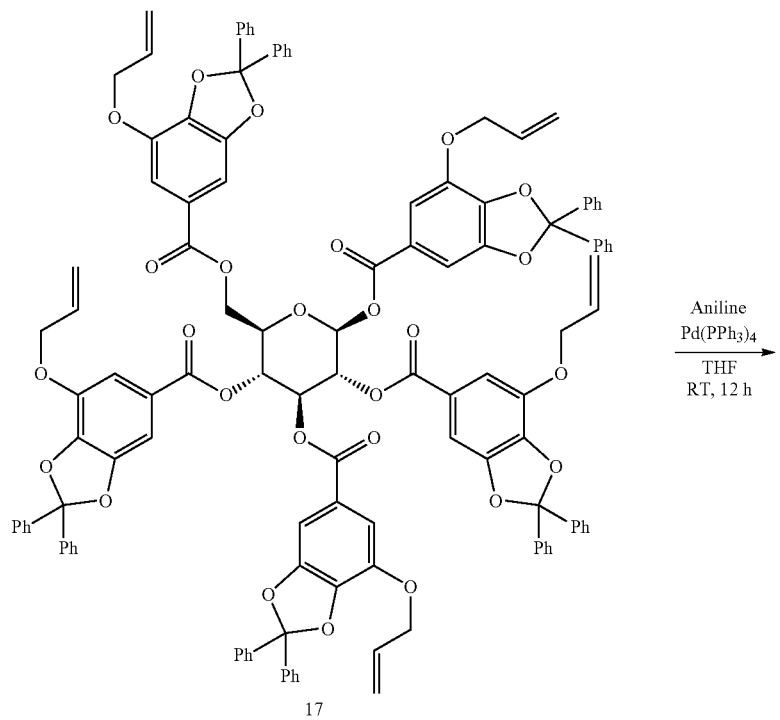

17

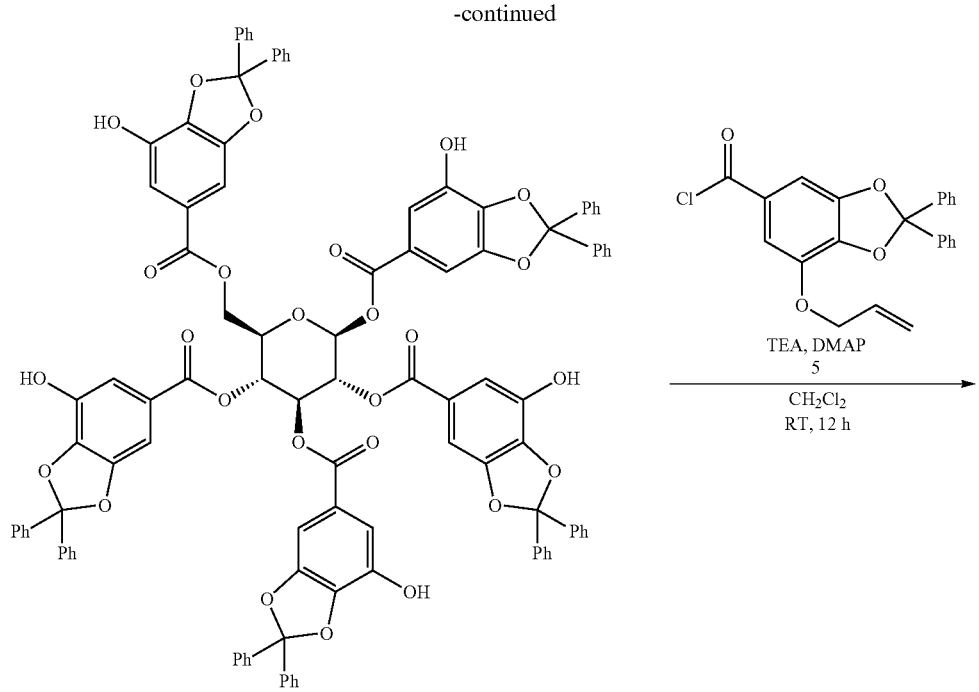
18
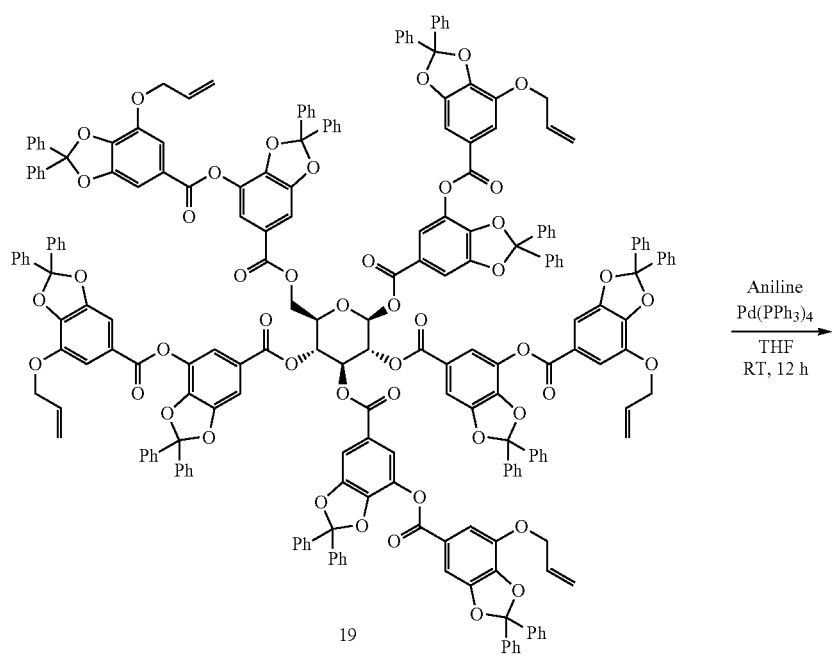
19

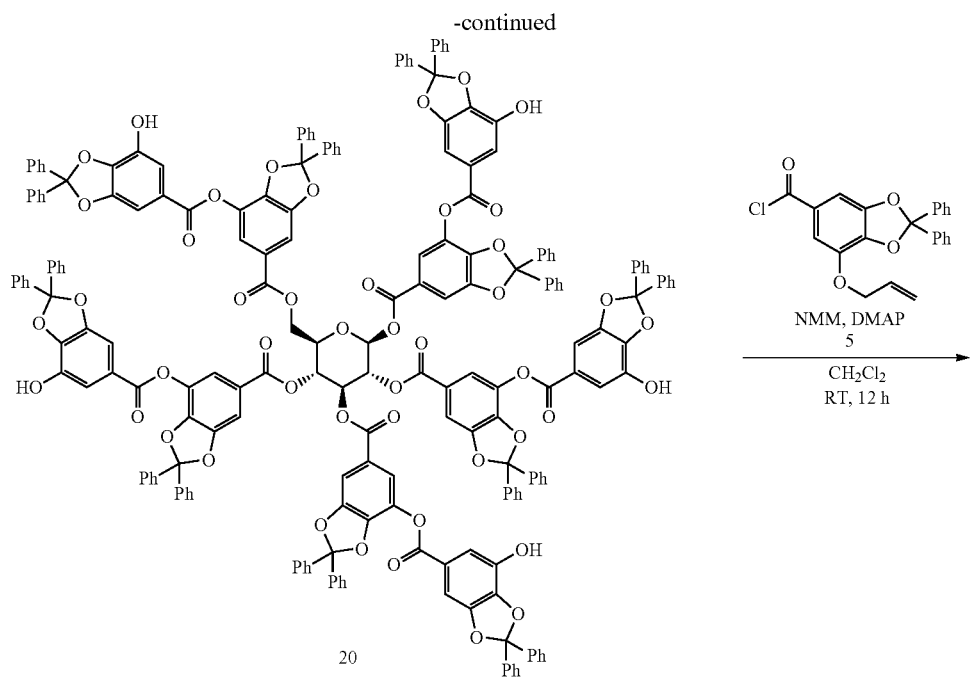
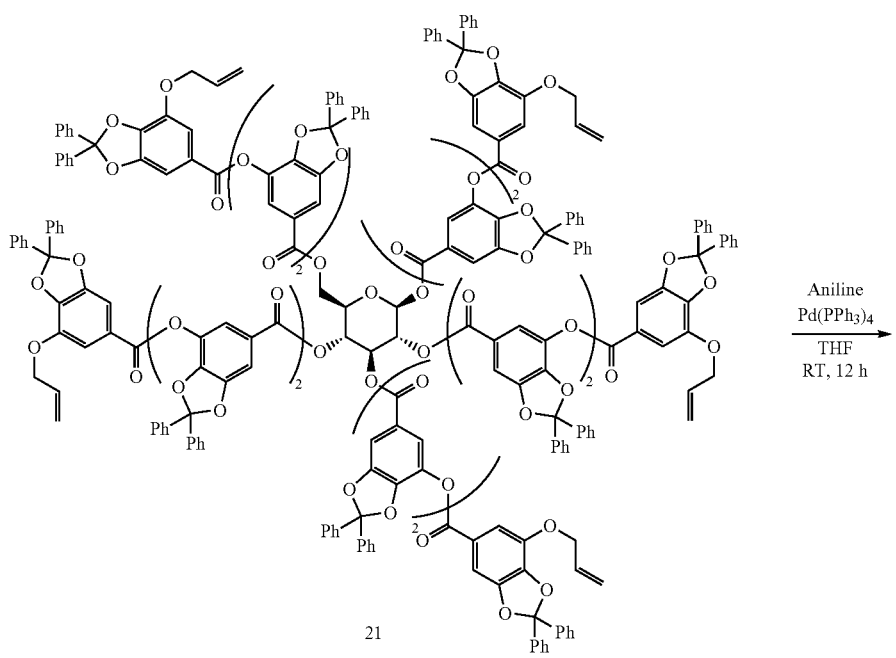

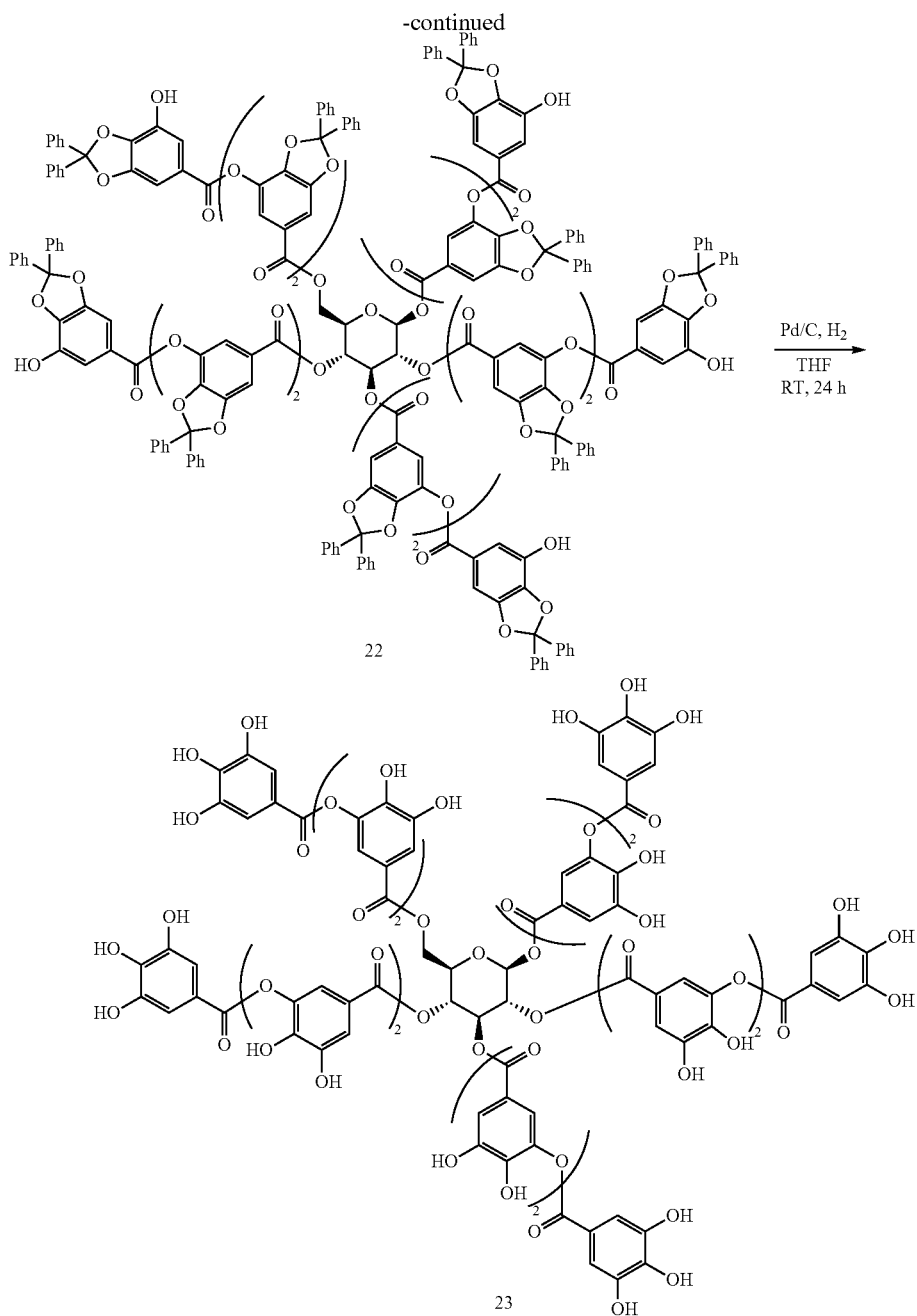

Preparation of β form of (2S,3R,4S,5R,6R)-6-(((7-(allyloxy)-2,2-diphenylbenzo[d][1,3]dioxole-5-carbonyl)oxy)methyl)tetrahydro-2H-pyran-2,3,4,5-tetrayl tetrakis(7-(allyloxy)-2,2-diphenylbenzo[d][1,3]dioxole-5-carboxylate) (17)

A mixture of 3-D-(+)-glucose (200.0 mg, 1.1 mmol), pyridine (1.3 mL, mmol) and the compound (5) (3.1 g, 7.8 mmol) in anhydrous acetonitrile (6.0 mL) was stirred at RT for 12 hrs. After the reaction was complete, the mixture was concentrated under vacuum. The residue was diluted with dichloromethane, extracted with water, washed with brine, dried over anhydrous magnesium sulfate and filtered. The filtrate was evaporated in vacuo. The residue was purified by flash column chromatography with silica gel and ethyl acetate/hexanes (1:2) to afford the compound (17) (1.1 g, 49%) as a white solid. $^1$H NMR (CDCl$_3$, 500 MHz) δ 7.56-7.04 (m, 60H), 6.05-5.89 (m, 6H), 5.82 (t, J=9.8 Hz, 1H), 5.63 (t, J=9.6 Hz, 1H), 5.56 (t, J=9.8 Hz, 1H), 5.40-5.27 (m, 5H), 5.25-5.14 (m, 5H), 4.68-4.52 (m, 10H), 4.27-4.23 (m, 1H), 4.20-4.18 (m, 1H).

Preparation of β form of (2S,3R,4S,5R,6R)-6-(((7-hydroxy-2,2-diphenylbenzo[d][1,3]dioxole-5-carbonyl)oxy)methyl)tetrahydro-2H-pyran-2,3,4,5-tetrayltetrakis(7-hydroxy-2,2-diphenylbenzo[d][1,3]dioxole-5-carboxylate) (18)

To a stirred solution of the compound (17) (1.0 g, 0.5 mmol) in dry tetrahydrofuran (5.0 mL) was added aniline (0.2 mL, 2.0 mmol) and tetrakis(triphenylphosphine)palladium (0.3 g, 0.3 mmol). The mixture was stirred at RT for 12 hrs. The mixture was filtered through Celite and the filtrate was concentrated in vacuo. The residue was purified by flash column chromatography with silica gel and ethyl acetate/hexanes (1:1) to afford the compound (18) (598.0 mg, 66%) as a white solid. $^1$H NMR (CDCl$_3$, 600 MHz) δ 7.52-6.93 (m, 60H), 6.13 (d, J=7.8H, 1H), 5.86 (t, J=9.0 Hz, 1H), 5.72-5.71 (m, 2H), 4.57 (d, J=10.8 Hz, 1H), 4.32 (m, 2H).

Preparation of β form of (2S,3R,4S,5R,6R)-2-((7-((7-(allyloxy)-2,2-diphenylbenzo[d][1,3]dioxole-5-carbonyl)oxy)-2,2-diphenylbenzo[d][1,3]dioxole-5-carbonyl)oxy)-6-(((7-((7-(allyloxy)-2,2-diphenylbenzo[d][1,3]dioxole-5-carbonyl)oxy)-2,2-diphenylbenzo[d][1,3]dioxole-5-carbonyl)oxy)methyl)tetrahydro-2H-pyran-3,4,5-triyltris(7-((7-(allyloxy)-2,2-diphenylbenzo[d][1,3]dioxole-5-carbonyl)oxy)-2,2-diphenylbenzo[d][1,3]dioxole-5-carboxylate) (19)

A mixture of the compound (18) (573.0 mg, 0.3 mmol), triethylamine (1.4 mL, 9.8 mmol) and 4-dimethylaminopyridine (20.0 mg, 0.2 mmol) and the compound (5) (1.3 g, 3.3 mmol) in dichloromethane (6.6 mL) was stirred at RT for 12 hrs. After the reaction was complete, the mixture was extracted with water, washed with brine, dried over anhydrous magnesium sulfate and filtered. The filtrate was evaporated in vacuo. The residue was purified by flash column chromatography with silica gel and ethyl acetate/hexanes (1:2) to afford the compound (19) (1.1 g, 96%) as a white solid. $^1$H NMR (CDCl$_3$, 600 MHz) δ 7.58-7.26 (m, 120H), 6.08 (d, J=8.4 Hz, 1H), 6.06-5.96 (m, 5H), 5.85 (t, J=9.6 Hz, 1H), 5.67 (dd, J=9.6, 8.5 Hz, 1H), 5.56 (t, J=9.7 Hz, 1H), 5.40-5.34 (m, 5H), 5.26-5.22 (m, 5H), 4.68-4.63 (m, 10H), 4.45 (d, J=10.8 Hz, 1H), 4.34 (dd, J=12.0, 4.8 Hz, 1H), 4.20-4.17 (m, 1H).

Preparation of β form of (2S,3R,4S,5R,6R)-6-(((7-((7-hydroxy-2,2-diphenylbenzo[d][1,3]dioxole-5-carbonyl)oxy)-2,2-diphenylbenzo[d][1,3]dioxole-5-carbonyl)oxy)methyl) tetrahydro-2H-pyran-2,3,4,5-tetrayltetrakis(7-((7-hydroxy-2,2-diphenylbenzo[d][1,3]dioxole-5-carbonyl)oxy)-2,2-diphenylbenzo[d][1,3]dioxole-5-carboxylate) (20)

To a stirred solution of the compound (19) (1.1 g, 0.3 mmol) in anhydrous tetrahydrofuran (6.0 mL) was added aniline (0.1 mL, 1.3 mmol) and tetrakis(triphenylphosphine)palladium (0.2 g, 0.2 mmol). The mixture was stirred at RT for 12 hrs. The mixture was filtered through Celite and the filtrate was concentrated in vacuo. The residue was purified by flash column chromatography with silica gel and ethyl acetate/hexanes (1:1) to afford the compound (20) (0.8 g, 76%) as a white solid. $^1$H NMR (CDCl$_3$, 600 MHz) δ 7.62-7.19 (m, 120H), 6.09 (d, J=8.4 Hz, 1H), 5.85 (t, J=9.6 Hz, 1H), 5.64 (t, J=9.6 Hz, 1H), 5.51 (t, J=9.6 Hz, 1H), 4.60 (dd, J=12.0, 3.6 Hz, 1H), 4.37-4.35 (m, 1H), 4.25-4.23 (m, 1H).

Preparation of β form of (2S,3R,4S,5R,6R)-6-(((7-((7-((7-(allyloxy)-2,2-diphenylbenzo [d][1,3]diox-ole-5-carbonyl)oxy)-2,2-diphenylbenzo[d][1,3]diox-ole-5-carbonyl)oxy)-2,2-diphenylbenzo[d][1,3] dioxole-5-carbonyl)oxy)methyl)tetrahydro-2H-pyran-2,3,4,5-tetrayl tetrakis(7-((7-((7-(allyloxy)-2, 2-diphenylbenzo[d][1,3]dioxole-5-carbonyl)oxy)-2, 2-diphenylbenzo[d][1,3]dioxole-5-carbonyl)oxy)-2, 2-diphenylbenzo[d][1,3]dioxole-5-carboxylate) (21)

A mixture of the compound (20) (789.0 mg, 0.2 mmol), N-methylmorpholine (0.8 mL, 7.1 mmol), 4-dimethylaminopyridine (14.0 mg, 0.1 mmol) and the compound (5) (927.0 mg, 2.4 mmol) in dichloromethane (2.4 mL) was stirred at RT for 12 hrs. After the reaction was complete, the mixture was extracted with water, washed with brine, dried over anhydrous magnesium sulfate and filtered. The filtrate was evaporated in vacuo. The residue was purified by flash column chromatography with silica gel and ethyl acetate/hexanes (1:2) to afford the compound (21) (600.0 mg, 50%) as a white solid. $^1$H NMR (CDCl$_3$, 400 MHz) δ 7.68-7.22 (m, 180H), 6.08-5.96 (m, 6H), 5.84 (t, J=9.5 Hz, 1H), 5.66 (t, J=8.9 Hz, 1H), 5.55 (t, J=9.6 Hz, 1H), 5.41-5.36 (m, 5H), 5.26-5.24 (m, 5H), 4.68-4.63 (m, 10H), 4.46 (d, J=11.4 Hz, 1H), 4.33-4.31 (m, 1H), 4.21-4.17 (m, 1H).

Preparation of β form of (2S,3R,4S,5R,6R)-6-(((7-((7-((7-hydroxy-2,2-diphenylbenzo [d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydro-2H-pyran-2,3,4,5-tetrayl tetrakis(7-((7-((7-hydroxy-2,2-diphenylbenzo [d][1,3]dioxole-5-carbonyl)oxy)-2,2-diphenylbenzo [d][1,3]dioxole-5-carbonyl)oxy)-2,2-diphenylbenzo [d][1,3]dioxole-5-carboxylate) (22)

To a stirred solution of the compound (21) (598.0 mg, 0.1 mmol) in anhydrous tetrahydrofuran (2.5 mL) was added aniline (0.04 mL, 0.8 mmol) and tetrakis(triphenyl phosphine)palladium (67.0 mg, 0.1 mmol) was added. The mixture was stirred at RT for 12 hrs. The mixture was filtered through Celite and the filtrate was concentrated in vacuo. The residue was purified by flash column chromatography with silica gel and ethyl acetate/hexanes (1:1) to afford the compound (22) (340.0 mg, 59%) as white solid. $^1$H NMR (CDCl$_3$, 600 MHz) δ 7.67-7.18 (m, 180H), 6.07 (d, J=7.8 Hz, 1H), 5.82 (t, J=9.6 Hz, 1H), 5.64 (t, J=9.0 Hz, 1H), 5.52 (t, J=9.6 Hz, 1H), 4.45 (d, J=10.2 Hz, 1H), 4.37-4.34 (m, 1H), 4.19-4.17 (m, 1H).

Preparation of β form of (2S,3R,4S,5R,6R)-6-(((3-((3,4-dihydroxy-5-((3,4,5-trihydroxybenzoyl)oxy) benzoyl)oxy)-4,5-dihydroxybenzoyl)oxy)methyl) tetrahydro-2H-pyran-2,3,4,5-tetrayl tetrakis(3-((3,4-dihydroxy-5-((3,4,5-trihydroxybenzoyl)oxy)benzoyl) oxy)-4,5-dihydroxybenzoate) (23)

To a stirred solution of the compound (22) (100.0 mg, 0.02 mmol) in dry THF (3.0 mL) was added 10 wt % Pd/C (100 mg). The mixture was stirred at RT under H$_2$ (8 atm) for 24 hrs. The mixture was then filtered through Celite, washed with acetone (10 mL) and the combined filtrates were evaporated in vacuo. The residue was precipitated with ethyl acetate/hexanes (1:25) to give the compound (23) as an off-white solid (21.0 mg, 42%). $^1$H NMR (MeOD, 600

MHz) δ 7.54-6.97 (m, 30H), 6.32 (s, 1H), 6.01 (s, 1H), 5.68 (s, 2H), 4.59-4.49 (m, 3H). ESI-MS, m/z 1229 $[M-2H]^{2-}$.

Example 6. In Vitro Measurements of Human D-Amino Acid Oxidase (hDAAO) Activity

The hDAAO inhibitory activities of Examples above were measured by using D-Serine as a substrate to produce $H_2O_2$. The produced $H_2O_2$ would be oxidized by peroxidase, and the produced free radicals would further react with Amplex Red reagent to emit fluorescence. The intensity of fluorescence at 590 nm would be measured to represent the activity of hDAAO. All compounds were dissolved in DMSO. Each compound was diluted with DMSO in 3-fold serial dilution to create a 9-point dose response curve. Each sample was added in triplicate, 1 μL/well, into 96-well black plates. Positive control wells were added with 1 μL of DMSO. Then 49 μL of assay buffer (100 mM Tris-HCl, pH 8.5) containing 1.2 ng/mL hDAAO, 900 nM FAD, 0.2 units/mL HRP, and 100 μM Amplex Red was added to each well of the plate using a multichannel pipette. Next, 50 μL of 100 mM D-Serine in assay buffer was added. The reaction plates were then incubated in the dark at room temperature. The fluorescence readout was detected at 0 and 20 minutes by Molecular Device Gemini EM fluorescence reader using the following settings: excitation filter 530 nm, and emission filter 590 nm. The percentage of inhibition values for each well was calculated with the following equation:

The percentage of inhibition=(fluorescence sample, 20 min−fluorescence sample, 0 min)/(fluorescence DMSO, 20 min−fluorescence DMSO, 0 min)×100%

The nonlinear curve fitting model in GraphPad Prism 5 was used to calculate $IC_{50}$ value for each compound. The results are shown in Table 1 and FIG. 1.

TABLE 1

The hDAAO IC$_{50}$ values of compounds of Formula (I)

| IC$_{50}$ | Compound 101 | Compound 102 | Compound 103 | Compound 13 | Compound 16 | Compound 23 |
|---|---|---|---|---|---|---|
| R$_{1-5}$ | (structure with single galloyl group) | (structure with digalloyl group) | (structure with trigalloyl group) | As illustrated in Example 3 | As illustrated in Example 4 | As illustrated in Example 5 |
| Galloyl Number | 5 | 5 | 10 | 15 | 20 | 15 |
| µg/mL | 0.050 ± 0.004 | 0.051 ± 0.002 | 0.033 ± 0.001 | 0.032 ± 0.001 | 0.035 ± 0.003 | 0.029 ± 0.002 |
| µM | 0.051 ± 0.004 | 0.053 ± 0.002 | 0.020 ± 0.001 | 0.013 ± 0.001 | 0.011 ± 0.001 | 0.012 ± 0.001 |

As illustrated in Table 1, there is a general trend that the more the galloyl moieties, the lower the $IC_{50}$ values in terms of μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one of skill in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of," "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A compound of formula (I):

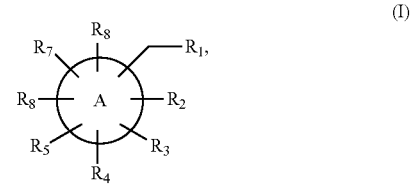

or a pharmaceutically acceptable salt thereof, wherein:
Ring A is a 5 to 8 membered monocyclic ring system, which optionally comprises at least one heteroatom selected from the group consisting of N, O, P, and S;
each of R1, R$_2$, R$_3$, R$_4$, R$_5$, R$_6$, R$_7$, and R$_8$, independently, is absent, or of the formula:

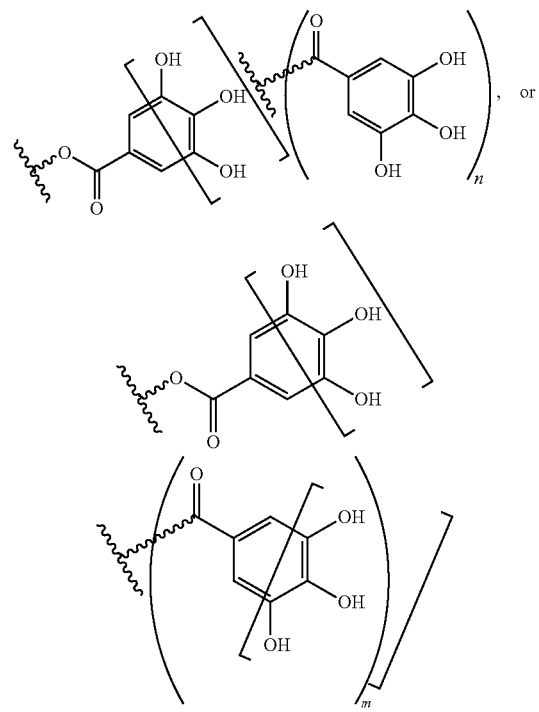

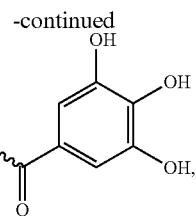

wherein at least one of R$_1$, R$_2$, R$_3$, R$_4$, R$_5$, R$_6$, R$_7$, and R$_8$ is present wherein R$_1$, R$_2$, R$_3$, R$_4$, R$_5$, R$_6$, R$_7$, or R$_8$ is optionally substituted with 1, 2, 3, 4, or 5 substituents selected from the group consisting of C1-3 alkyl, halogen, —CN, —NO2, —SH, -S(C$_{1-3}$ alkyl), —NH$_2$, NH(C$_{1-3}$alkyl), N(C$_{1-3}$ alkyl)2, and –O(C$_{1-3}$ alkyl); and wherein n is 0 or 1;

m is 1, 2, 3, 4, or 5; and the total number of galloyl moieties is an integer of 15 to 35, inclusive.

2. The compound of claim 1, wherein Ring A is:

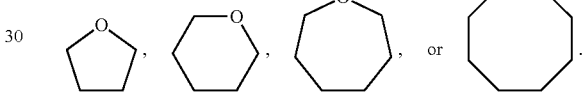

3. The compound of claim 2, wherein each of R$_1$, R$_2$, R$_3$, R$_4$, R$_5$, R$_6$, R$_7$, and R$_8$, independently, is of the formula:

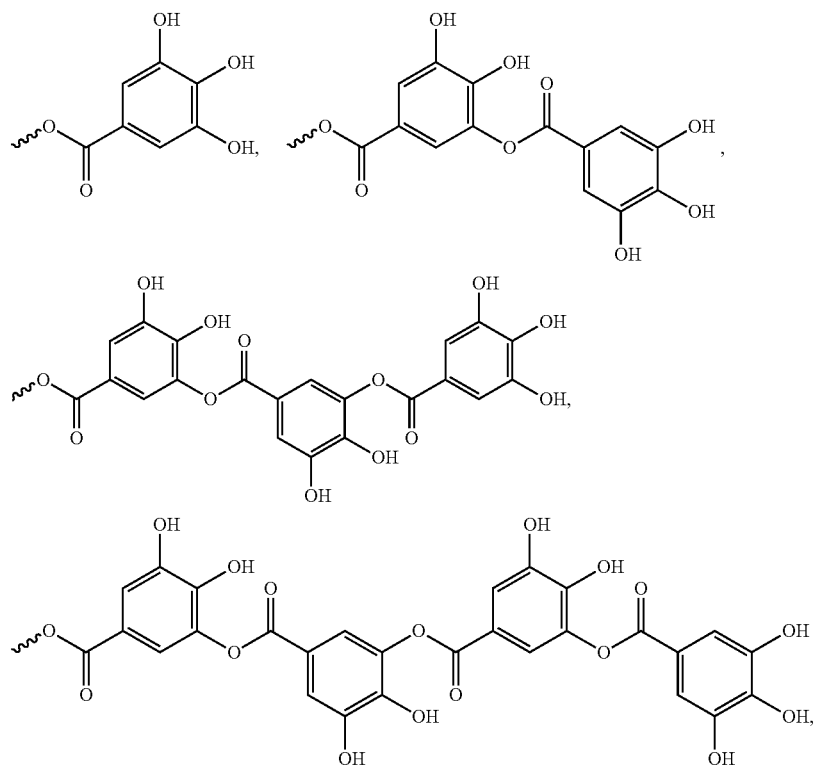

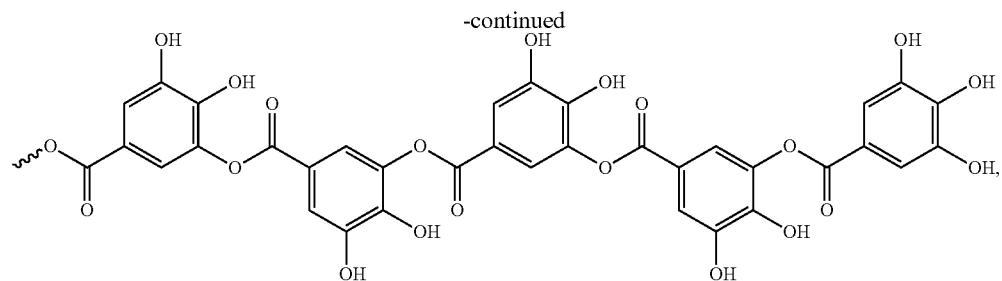
or absent.
4. The compound of claim 3, wherein the compound of Formula (I) is of the formula:
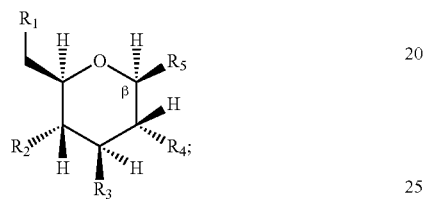
and $R_1$, $R_2$, $R_3$, $R_4$, and $R_5$ are each selected from the group consisting of:
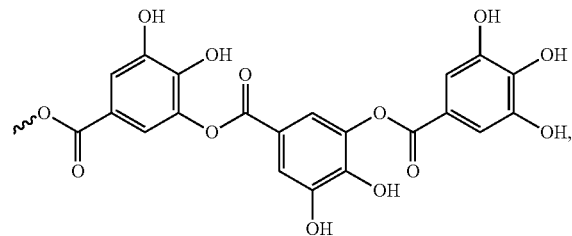
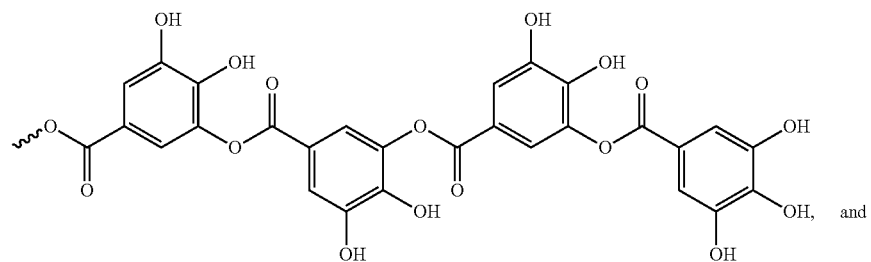
and
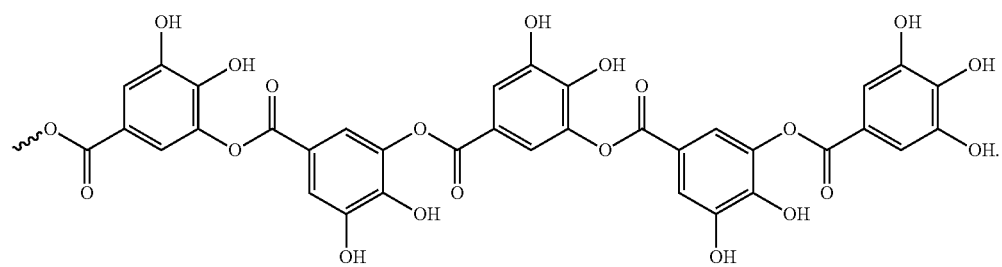

5. The compound of claim 3, wherein the compound of Formula (I) is of the formula:

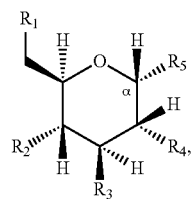

and $R_1$, $R_2$, $R_3$, $R_4$, and $R_5$ are each selected from the group consisting of:

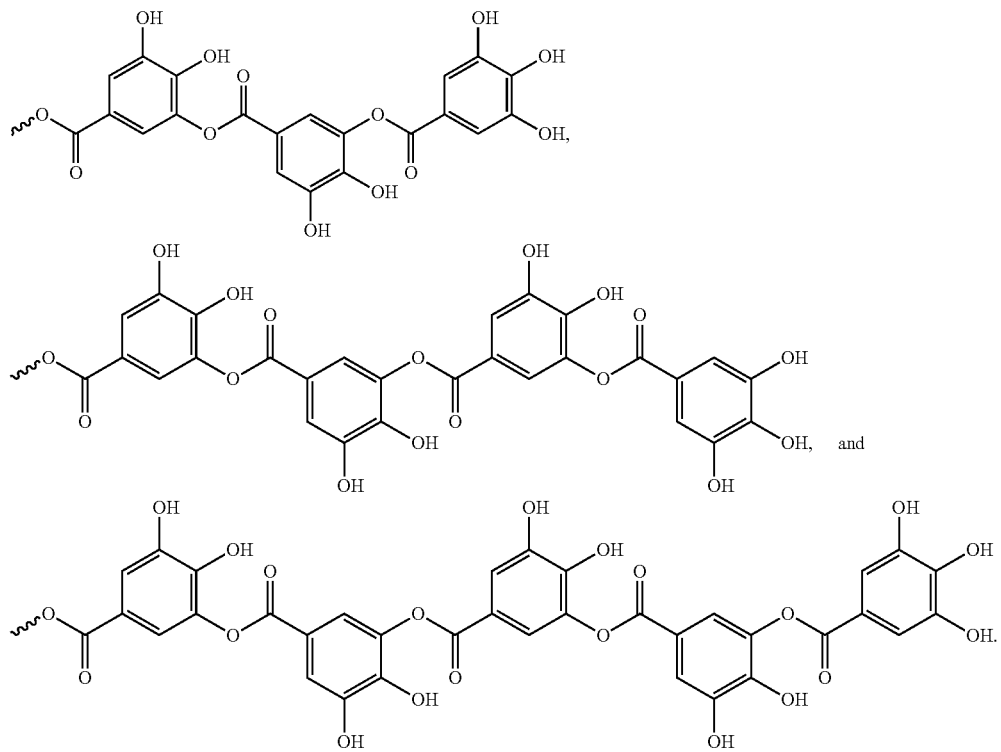

6. A composition comprising the compound of claim 1 and a carrier.

7. The composition of claim 6, wherein the composition is a pharmaceutical composition, a nutraceutical composition, a health food, or a medical food.

8. A method for preparing the compound of claim 1, comprising:
（a) providing a compound of formula (Ia)

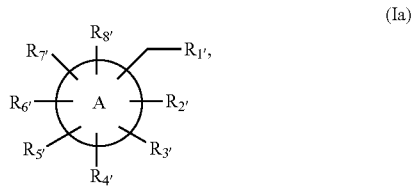

wherein $R_{1'}$, $R_{2'}$, $R_{3'}$, $R_{4'}$, $R_{5'}$, $R_{6'}$, $R_{7'}$, and $R_{8'}$, independently, are each —OH, —NH$_2$ or absent;
wherein at least one of $R_{1'}$, $R_{2'}$, $R_{3'}$, $R_{4'}$, $R_{5'}$, $R_{6'}$, $R_{7'}$, and $R_{8'}$ is present; and wherein Ring A is a 5 to 8 membered monocyclic ring system, which optionally comprises at least one heteroatom selected from the group consisting of N, O, P, and S;

(b) reacting the compound of formula (Ia) with 7-(allyloxy)-2,2-diphenylbenzo [d][1,3]dioxole-5-carbonyl chloride, to allow conjugation of 7-(allyloxy)-2,2-diphenylbenzo [d][1,3]dioxole-5-carbonyl chloride to one or more of $R_{1'}$, $R_{2'}$, R3', R4', R5', $R_{6'}$, $R_{7'}$, and $R_{8'}$ of the compound of formula (Ia), thereby producing a first intermediate; and (c) de-protecting the allyl groups and the cyclic acetal groups in 7-(allyloxy)-2,2-diphenylbenzo [d][1,3]dioxole-5-carbonyl chloride that is conjugated to the compound of Formula (Ia) to obtain the compound of claim 1.

9. The method of claim 8, wherein step (c) is performed by:
(c1) de-protecting the allyl groups;
(c2) de-protecting the cyclic acetal groups.

10. The method of claim 9, further comprising, prior to step (c2), repeating the process consisting of steps (b) and (c1) for 3-7 times.

11. The method of claim 8, wherein Ring A is:

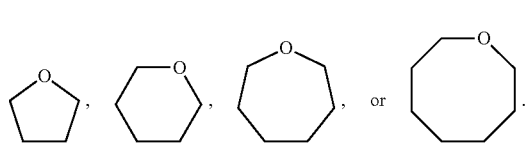

12. The method of claim 8, wherein the compound of formula (Ia) is glucose.

13. The method of claim 12, the glucose is in α form or in β form.

14. The method of claim 8, further comprising purifying the compound of claim 1 produced after step (c).

15. The compound of claim 1, which is of the formula:
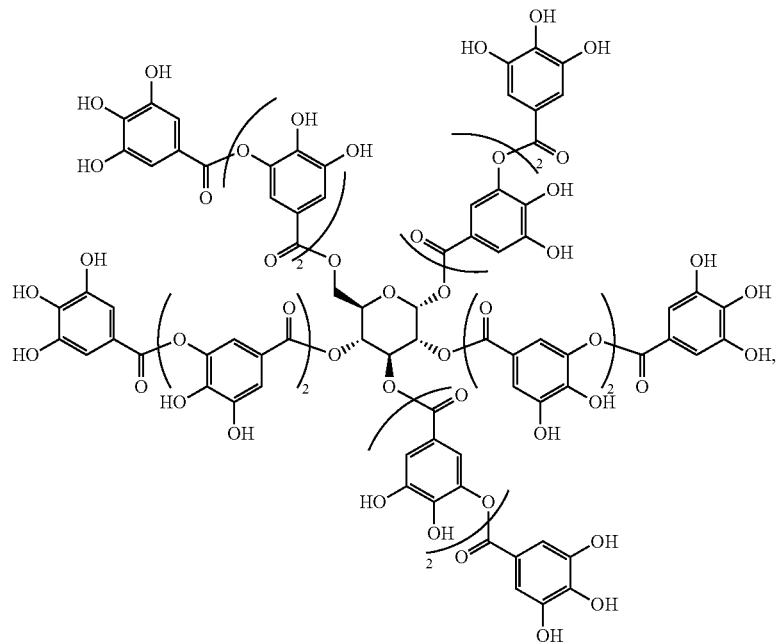
or a pharmaceutically acceptable salt thereof.
* * * * *

UNITED STATES PATENT AND TRADEMARK OFFICE
CERTIFICATE OF CORRECTION

PATENT NO. : 10,927,138 B2
APPLICATION NO. : 15/991710
DATED : February 23, 2021
INVENTOR(S) : Guochuan Emil Tsai et al.

Page 1 of 1

It is certified that error appears in the above-identified patent and that said Letters Patent is hereby corrected as shown below:

In the Claims

Column 90, at Lines 60-65:

Please delete " 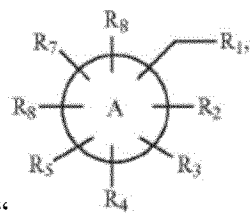 " and replace with 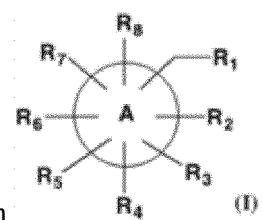

Column 92, at Line 15:
Please delete "C1-3" and replace with $C_{1-3}$

Column 92, at Line 16:
Please delete "–NO2" and replace with -$NO_2$

Column 92, at Line 17:
Please delete "N($C_{1-3}$ alkyl)2" and replace with N($C_{1-3}$ alkyl)$_2$ Column 96, at Line 8:
Please delete "R3', R4', R5'" and replace with $R_{3'}$, $R_{4'}$, $R_{5'}$ Signed and Sealed this
Seventh Day of December, 2021

Drew Hirshfeld
*Performing the Functions and Duties of the
Under Secretary of Commerce for Intellectual Property and
Director of the United States Patent and Trademark Office*